US012685947B2

(12) United States Patent
Lee

(10) Patent No.: US 12,685,947 B2
(45) Date of Patent: Jul. 21, 2026

(54) METHODS OF AND SYSTEMS FOR A DRY MILLING PROCESS WITH TWO STEPS LIQUEFICATIONS

(71) Applicant: Lee Tech LLC, Los Gatos, CA (US)

(72) Inventor: Chie Ying Lee, Los Gatos, CA (US)

(73) Assignee: Lee Tech LLC, Los Gatos, CA (US)

( * ) Notice: Subject to any disclaimer, the term of this patent is extended or adjusted under 35 U.S.C. 154(b) by 0 days.

(21) Appl. No.: 18/115,586

(22) Filed: Feb. 28, 2023

(65) Prior Publication Data

US 2023/0277956 A1 Sep. 7, 2023

Related U.S. Application Data

(60) Provisional application No. 63/315,431, filed on Mar. 1, 2022.

(51) Int. Cl.
| | |
|---|---|
| *B01D 3/00* | (2006.01) |
| *A23K 10/38* | (2016.01) |
| *C11B 13/00* | (2006.01) |
| *C12P 7/06* | (2006.01) |

(52) U.S. Cl.
CPC .............. *B01D 3/001* (2013.01); *A23K 10/38* (2016.05); *C11B 13/00* (2013.01); *C12P 7/06* (2013.01)

(58) Field of Classification Search
CPC ......... B01D 3/001; A23K 10/38; C11B 13/00; C12P 7/06
USPC .......................................................... 426/54
See application file for complete search history.

(56) References Cited

U.S. PATENT DOCUMENTS

| | | |
|---|---|---|
| 1,942,943 A | 1/1934 | Schnabel |
| 2,190,176 A | 2/1940 | Smith |
| 2,313,275 A | 3/1943 | Schopmeyer et al. |
| 2,600,903 A | 6/1952 | Miller |
| 2,967,107 A | 1/1961 | Geiger et al. |
| 3,054,676 A | 9/1962 | Lauhoff et al. |
| 3,058,887 A | 10/1962 | Platt et al. |
| 3,753,723 A | 8/1973 | Henderson |
| 3,786,078 A | 1/1974 | Smith et al. |
| 3,827,423 A | 8/1974 | Bolitho |
| 3,973,043 A | 8/1976 | Lynn |
| 3,975,546 A | 8/1976 | Stahmann |
| 4,042,172 A | 8/1977 | Norzdrovsky |
| 4,130,553 A | 12/1978 | Batley, Jr. |
| 4,171,383 A | 10/1979 | Chwalek et al. |
| 4,255,518 A | 3/1981 | Muller et al. |
| 4,313,061 A | 1/1982 | Thomas |
| 4,333,871 A | 6/1982 | De Jong |
| 4,341,713 A | 7/1982 | Stolp et al. |
| 4,361,651 A | 11/1982 | Keim |
| 4,396,161 A | 8/1983 | Roukolainen et al. |
| 4,517,022 A | 5/1985 | Harvey |
| 4,635,864 A | 1/1987 | Peterson et al. |

| | | |
|---|---|---|
| 4,772,481 A | 9/1988 | Rohwer |
| 4,835,100 A | 5/1989 | Dixon |
| 4,857,325 A | 8/1989 | Albeck |
| 4,978,618 A | 12/1990 | Kalina |
| 5,177,008 A | 1/1993 | Kampen |
| 5,244,159 A | 9/1993 | Newman |
| 5,248,099 A | 9/1993 | Lahner et al. |
| 5,294,434 A | 3/1994 | King |
| 5,364,335 A | 11/1994 | Franzen et al. |
| 5,475,099 A | 12/1995 | Knauf |
| 5,516,974 A | 5/1996 | Sasae |
| 5,994,113 A | 11/1999 | Kauppinen et al. |
| 6,080,401 A | 6/2000 | Reddy |
| 6,190,462 B1 | 2/2001 | Markland et al. |
| 6,254,914 B1 | 7/2001 | Singh et al. |
| 6,274,358 B1 | 8/2001 | Holtz et al. |
| 6,569,653 B1 | 5/2003 | Alard |
| 6,899,910 B2 | 5/2005 | Johnston et al. |
| 7,297,236 B1 | 11/2007 | Vander Griend |
| 7,563,469 B1 | 7/2009 | Navarro et al. |
| 7,687,648 B2 | 3/2010 | Smallridge et al. |
| 7,700,094 B1 | 4/2010 | Nsereko |
| 7,858,140 B2 | 12/2010 | Paustian et al. |
| 9,012,191 B2 | 4/2015 | Lee |
| 9,352,326 B2 | 5/2016 | Lee |

(Continued)

FOREIGN PATENT DOCUMENTS

| | | |
|---|---|---|
| AU | 2013200519 B2 | 2/2013 |
| CN | 1883299 A | 12/2006 |

(Continued)

OTHER PUBLICATIONS

Google Search Result (Retrieved on May 22, 2024) (Year: 2024).*
The Second Office Action dated Mar. 25, 2023 from Chinese Patent Application No. 202080073152.8.
The Notice of Rejection Decision dated May 27, 2023 from Chinese Patent Application No. 202080073152.8.
The Notification of Transmittal of International Search Report and the Written Opinion of the International Searching Authority, or the Declaration dated Jul. 19, 2023 from PCT Patent Application No. PCT/US23/14159.
International Search Report mailed Aug. 23, 2023, International Application No. PCT/US2023/018136, 20 pages.
The Office Action dated Jan. 26, 2024 for Chinese Patent Application No. 202280017556.4.
The Notification of Transmittal of International Search Report and the Written Opinion of the International Searching Authority, or the Declaration dated Oct. 11, 2023, from PCT Patent Application No. PCT/US23/25624.

(Continued)

*Primary Examiner* — Erik Kashnikow
*Assistant Examiner* — Bhaskar Mukhopadhyay
(74) *Attorney, Agent, or Firm* — Haverstock & Owens

(57) ABSTRACT

The present disclosure provides a two-step liquefication (e.g., using a high (>23 Be) and a low Be (<5 Be) liquid media) process in a dry milling process/plant. The dry milling process comprises liquifying starch from milled corns making a liquefied starch slurry in a first liquefication tank having a slurry >23 Be, performing a first solid/liquid separation using a first paddle screen after the liquifying starch, soaking, cooking, or degrading protein in a second liquefication tank with a slurry <5 Be, and performing a second solid/liquid separation using a second paddle screen after the soaking, cooking, or degrading protein in a second liquefication tank.

10 Claims, 14 Drawing Sheets

(56)  References Cited

U.S. PATENT DOCUMENTS

| | | |
|---|---|---|
| 9,388,475 B2 | 7/2016 | Lee |
| 9,695,381 B2 | 7/2017 | Lee |
| 9,777,303 B2 | 10/2017 | Jakel et al. |
| 10,190,086 B2 | 1/2019 | Narendranath |
| 11,166,478 B2 | 11/2021 | Lee |
| 11,427,839 B2 | 8/2022 | Lee |
| 11,680,278 B2 | 6/2023 | Lee |
| 12,065,513 B2 | 8/2024 | Lee |
| 12,084,707 B2 | 9/2024 | Lee |
| 12,351,852 B2 | 7/2025 | Lee |
| 12,365,744 B2 | 7/2025 | Lee |
| 2001/0014360 A1 | 8/2001 | Paluch |
| 2002/0122944 A1 | 9/2002 | Ogle et al. |
| 2003/0180415 A1* | 9/2003 | Stiefel ................... A23K 10/30 |
| | | 426/18 |
| 2004/0009160 A1 | 1/2004 | Villamar |
| 2004/0071757 A1 | 4/2004 | Rolf |
| 2004/0087808 A1 | 5/2004 | Prevost et al. |
| 2004/0187863 A1 | 9/2004 | Langhauser |
| 2004/0258782 A1 | 12/2004 | Hoffman et al. |
| 2005/0009133 A1 | 1/2005 | Johnston et al. |
| 2005/0028810 A1 | 2/2005 | Lee |
| 2005/0100996 A1 | 5/2005 | Antero, Jr. et al. |
| 2005/0170067 A1 | 8/2005 | Shao et al. |
| 2005/0249837 A1 | 11/2005 | Massimio et al. |
| 2005/0281792 A1 | 12/2005 | Short |
| 2006/0127453 A1 | 6/2006 | Harel |
| 2006/0154353 A1 | 7/2006 | Duan |
| 2006/0292677 A1 | 12/2006 | Ostrander |
| 2007/0066476 A1 | 3/2007 | Ullmann |
| 2007/0148318 A1 | 6/2007 | Rubio et al. |
| 2007/0184159 A1 | 8/2007 | Shima et al. |
| 2007/0184541 A1 | 8/2007 | Karl et al. |
| 2007/0210007 A1 | 9/2007 | Scheimann et al. |
| 2007/0231311 A1 | 10/2007 | Kroening |
| 2008/0095881 A1 | 4/2008 | Ber |
| 2008/0210541 A1 | 9/2008 | Wenger et al. |
| 2008/0279983 A1* | 11/2008 | Lohrmann .............. C08B 30/04 |
| | | 426/44 |
| 2009/0029432 A1 | 1/2009 | Abbas et al. |
| 2009/0047382 A1* | 2/2009 | Cates ........................ C12P 7/06 |
| | | 426/14 |
| 2009/0061490 A1 | 3/2009 | Edwards et al. |
| 2009/0093027 A1 | 4/2009 | Balan et al. |
| 2009/0181153 A1 | 7/2009 | Bendorf et al. |
| 2009/0227004 A1 | 9/2009 | Dale |
| 2010/0028484 A1 | 2/2010 | Kriesler et al. |
| 2010/0082312 A1 | 4/2010 | Macharia |
| 2010/0093860 A1 | 4/2010 | Boon et al. |
| 2010/0120128 A1 | 5/2010 | Liang |
| 2010/0159547 A1 | 6/2010 | Falcounbridge |
| 2010/0159552 A1 | 6/2010 | Benson et al. |
| 2010/0196994 A1 | 8/2010 | Van Leeuwen et al. |
| 2010/0260918 A1 | 10/2010 | Wang |
| 2010/0324274 A1 | 12/2010 | DeFrees |
| 2011/0086149 A1 | 4/2011 | Bootsma |
| 2011/0100359 A1 | 5/2011 | North |
| 2011/0106277 A1 | 5/2011 | Sayyar-Rodsari |
| 2011/0123657 A1 | 5/2011 | Vandenbroucke et al. |
| 2011/0100853 A1 | 6/2011 | Mann et al. |
| 2011/0177560 A1 | 7/2011 | Galvez, III et al. |
| 2011/0223307 A1 | 9/2011 | Bertoldo de Barros et al. |
| 2011/0250310 A1 | 10/2011 | Mateus |
| 2011/0250312 A1 | 10/2011 | Lewis |
| 2011/0269185 A1 | 11/2011 | David |
| 2011/0283602 A1 | 11/2011 | Gallop et al. |
| 2011/0315541 A1 | 12/2011 | Xu |
| 2012/0048716 A1 | 3/2012 | Sonnek |
| 2012/0077232 A1 | 3/2012 | Budaraju et al. |
| 2012/0077244 A1 | 3/2012 | Budaraju et al. |
| 2012/0107454 A1 | 5/2012 | Hoffman et al. |
| 2012/0125859 A1 | 5/2012 | Collins |
| 2012/0168387 A1 | 7/2012 | Tran et al. |
| 2012/0183643 A1 | 7/2012 | Dale |
| 2012/0199531 A1 | 8/2012 | Winsness |

| | | |
|---|---|---|
| 2012/0244590 A1 | 9/2012 | Lee |
| 2012/0245123 A1 | 9/2012 | Lopez Pedrosa et al. |
| 2012/0252065 A1 | 10/2012 | Rozenszain et al. |
| 2012/0270275 A1 | 10/2012 | Fenton et al. |
| 2013/0121891 A1 | 5/2013 | Dieker |
| 2013/0130343 A1 | 5/2013 | Purtle et al. |
| 2013/0206342 A1 | 8/2013 | Dahmes |
| 2013/0224333 A1 | 8/2013 | Nanjundaswamy et al. |
| 2013/0236936 A1* | 9/2013 | Lee ........................... A23J 1/12 |
| | | 426/495 |
| 2013/0288376 A1 | 10/2013 | Lee |
| 2013/0316041 A1 | 11/2013 | Maranz |
| 2013/0337517 A1 | 12/2013 | Razavi-Shirazi |
| 2013/0344045 A1 | 12/2013 | Faure |
| 2014/0004571 A1 | 1/2014 | Garrett |
| 2014/0053829 A1* | 2/2014 | Lee ........................... C13K 1/02 |
| | | 554/8 |
| 2014/0102950 A1 | 4/2014 | Bethke |
| 2014/0186868 A1 | 7/2014 | Siegert |
| 2014/0206055 A1 | 7/2014 | Ramos |
| 2014/0242251 A1 | 8/2014 | Bootsma |
| 2014/0273140 A1 | 9/2014 | Langhouser |
| 2014/0319066 A1 | 10/2014 | LoCascio |
| 2014/0343254 A1 | 11/2014 | Gerardi |
| 2015/0152372 A1 | 6/2015 | Kohl |
| 2015/0176034 A1 | 6/2015 | Ramos |
| 2015/0223493 A1 | 8/2015 | Lee |
| 2015/0231535 A1 | 8/2015 | Lee et al. |
| 2015/0240266 A1 | 8/2015 | Lee |
| 2015/0307822 A1 | 10/2015 | Rossell et al. |
| 2016/0060658 A1 | 3/2016 | Lee |
| 2016/0222135 A1* | 8/2016 | Lee ........................... C12P 7/16 |
| 2016/0374364 A1 | 12/2016 | Lee |
| 2017/0022529 A1 | 1/2017 | Jakel et al. |
| 2017/0058300 A1 | 3/2017 | Aurandt |
| 2017/0166834 A1 | 6/2017 | Jakel |
| 2017/0166835 A1 | 6/2017 | Jakel |
| 2018/0044620 A1 | 2/2018 | Bootsma |
| 2018/0225669 A1 | 8/2018 | Brotherson |
| 2018/0343891 A1 | 12/2018 | Lee |
| 2019/0017080 A1 | 1/2019 | Bootsma |
| 2019/0119711 A1 | 4/2019 | Lee |
| 2019/0211365 A1 | 7/2019 | Jakel |
| 2019/0241834 A1 | 8/2019 | Lee |
| 2021/0024964 A1 | 1/2021 | Lee |
| 2021/0059277 A1 | 3/2021 | Lee |
| 2021/0113966 A1 | 4/2021 | Benson et al. |
| 2022/0022492 A1 | 1/2022 | Lee |
| 2022/0205006 A1 | 6/2022 | Cao et al. |
| 2022/0235150 A1 | 7/2022 | Lee |
| 2022/0348969 A1 | 11/2022 | Lee |
| 2023/0272437 A1 | 8/2023 | Lee |
| 2023/0277956 A1 | 9/2023 | Lee |
| 2023/0285979 A1 | 9/2023 | Lee |
| 2023/0406963 A1 | 12/2023 | Lee |
| 2024/0417761 A1 | 12/2024 | Lee |
| 2025/0043030 A1 | 2/2025 | Lee |
| 2025/0320530 A1 | 10/2025 | Lee |

FOREIGN PATENT DOCUMENTS

| | | |
|---|---|---|
| CN | 1966706 A | 5/2007 |
| CN | 101080483 A | 11/2007 |
| CN | 101453884 A | 8/2009 |
| CN | 101621935 A | 1/2010 |
| CN | 101795578 A | 8/2010 |
| CN | 102448321 A | 5/2012 |
| CN | 104703957 A | 6/2015 |
| CN | 106615685 A | 5/2017 |
| CN | 107034240 A | 8/2017 |
| CN | 107208116 A | 9/2017 |
| CN | 107208166 A | 9/2017 |
| DE | 4239342 A1 | 5/1994 |
| EP | 0772978 B1 | 11/1991 |
| EP | 722669 B1 | 5/2002 |
| GB | 511525 A | 8/1939 |
| GB | 852995 A | 11/1960 |
| WO | 01/14595 A2 | 3/2001 |
| WO | 2006104504 A2 | 10/2006 |

(56) References Cited

FOREIGN PATENT DOCUMENTS

| | | | | | |
|---|---|---|---|---|---|
| WO | 2012075481 | A1 | 6/2012 | | |
| WO | 2012145230 | A1 | 10/2012 | | |
| WO | 2012160191 | A2 | 11/2012 | | |
| WO | 2012166290 | A1 | 12/2012 | | |
| WO | 2013034747 | A1 | 3/2013 | | |
| WO | 2014031700 | A2 | 2/2014 | | |
| WO | 20140127852 | A2 | 8/2014 | | |
| WO | WO-2015066669 | A1 | * | 5/2015 | ............ C12P 19/02 |
| WO | 2016033548 | A1 | 3/2016 | | |
| WO | 2016123258 | A1 | 8/2016 | | |
| WO | 2021086865 | A1 | 5/2021 | | |
| WO | 2022159719 | A1 | 7/2022 | | |

OTHER PUBLICATIONS

The second Office Action, dated Aug. 1, 2023, from Chinese Patent Application No. 202080070146.7.

The Rejection Decision dated Mar. 29, 2024 for Chinese Patent Application No. 202080070146.7.

The Notice of Allowance dated Apr. 4, 2024 for Chinese Patent Application No. 202280017556.4.

The International Preliminary report on Patentability dated Dec. 26, 2024 for PCT Application No. PCT/US2023/025624.

The Notification Concerning Transmittal of International Preliminary report on Patentability dated Sep. 12, 2024 for PCT Application No. PCT/US2023/014159.

The International Preliminary report on Patentability dated Oct. 23, 2025 for International Application No. PCT/US2023/018136.

The Re-Examination Notice, mailed on Jan. 14, 2026, Chinese Patent Application No. 202080073152.8, 3 pages.

2nd Office Action from Chinese Patent Application No. 202380047671. 0, mailed on Nov. 2, 2025.

The Office Action dated Jul. 25, 2025 from Brazilian Patent Application No. BR112022008178-2.

The Office Action dated Jul. 27, 2025 from Chinese Patent Application No. 202380047671.0.

The Examiner's Report dated Dec. 11, 2025, from Canadian Application No. 3,159,554.

The Rejection Decision mailed on Jan. 4, 2026, from Chinese Patent Application No. 202380047671.0, 7 pages.

International Search Report and Written Opinion from PCT Application No. PCT/US15/47577.

"Organic" organic.org; published Dec. 25, 2012, accessed on Mar. 3, 2017, available at htt://web.archive.org/web/20121225201858/http://www.organic.org/home /faq.

Alfagreen supreme: available at:https://web.archive.org/web/2012120705040902/thttp://www.alfagreensupreme.com. burproducts:html:published Jul. 12, 2012, accessed on Mar. 6, 2017.

Egg, whole,raw, fresh form composition of Foods Raw, Processed, Prepared , USDA National Nutrient Database for Standard Reference, Release 22, Sep. 2009,; available at :http:// www.ars.usda. gov/northweast-area/beltsville-human-nutrition-research-center/nutrient-data-laboratory/docs/sr22-download-files/: access on Oct. 17, 2017.

Swiss chard, What's New and Beneficial About Swiss Chard: The World's Healthiest Foods; available at : http://web.archive.org/web/20130117060212/http://www.whfoods.com/genpage.php?tname=foodspice&dbid=16;published on Jan. 17, 2013: accessed on Oct. 19, 20174.

Singh et al., "Effect of Corn Oil on Thin Stillage Evaporators", Cereal Chemistry, pp. 846-849, 1999.

Blog, Birdworms & Buttermilk, Extracting Chlorophyll from Leafy Greens; available at: http://birdworms.com/2010/06/26/extractingchlorophyllfromleafygreens/; accessed on Oct. 6, 2016; published on Jun. 2010.

Timbekova et al., Chemistry and Biological Activity of Triterpenoid glycosides from Medicago available at: Saponins used in Food and Agriculture pp. 171-182, 1996.

Gonzalez-Martin, Use of NIRS technology with a remote reflectance fibre-optic probe for predicting mineral composition(Ca, K, P, Fe, Mn, Na, Zn), protein and moisture in alfalfa; Anal Bioanal Chem (2007) 387:2199-2205.

What Are Enzymes ?: published Mar. 7, 2013; available at : https://web.archive.org./webs/20130307025120/hrrp://www.enzyme-facts.com/enzymes.html; accessed on Aug. 11, 2017.

"hydrocarbon." In The Columbia Encyclopedia, by Paul Lagasse, and Columbia University. 7th ed. Columbia University Press, 2017. http://search.credoreference.com/content/entry/columency/hydrocarbon/0?institutionld=743.

"starch." In The American Heritage (R) Dictionary of the English Language, edited by The Editors of the American Heritage Dictionaries. 5th ed. Houghton Mifflin, 2011. http://search.credoreference.com/content/entry/hmdictenglang/starch/0?institutionld=743.

Kung, A review on silage additives and enzymes, Proceeding of the 59th Minneapolis Nutrition Conference, Sep. 1998; p. 121-135.

Heist, A Guide to Successful Yeast Propagation, Ethanol Producer Magazine, 2008.

Dotty 1, New natural medical antibiotic; Chlorophyll & Spinach, available at http://www.acne.org/messageboard/topic/254668-new-natural-medical-antibiotic-chlorophyllspinach/; published Nov. 30, 2009; accessed on Jul. 3, 2017.

Spinach, vol. 1, No. 14, University of the District of Columbia, Center for Nutrition, Diet and Health, published Jan. 23, 2014, accessed on Jul. 30, 2017, available at : https://web.archive.org/web/20140123214335/https://www.udc.edu/docs/causes/online/Spinach%2014.pdf.

Shahina Z. et al., "Variation of Protease Production by the Bacteria (Bacillus Fastidiosus) and the Fungus (Aspergillus Funiculosus)", Journal of Microbiology Research [online], 2013 [retrieved on Oct. 17, 2016], vol. 3, issue 1, retrieved from the Internet: <DIO: 10.5923//j.microbiology.2013030402>, pp. 135-142, see entire documents, especially p. 135.

International Search Report from PCT/US16/38436 dated Oct. 31, 2016.

The International Search Report dated Dec. 18, 2018, for International Application No. PCT/US18/56340.

The Office Action for Canadian Patent Application No. 2,951,715 dated Jul. 9, 2019.

The Office Action for Brazilian Patent Application No. BR112015003793-3 dated Jul. 23, 2019.

The Office Action dated May 9, 2019 for Canadian Patent Application No. 2,882,173.

The Brazilian Office Action for Patent Application No. BR112017016172-9 Dated: 26, 2019.

The Brazilian Office Action for Patent Application No. BR112017027884-7 Dated: Jan. 2, 2020.

The International Preliminary Report form PCT Application No. PCT/US2018/056340, dated Apr. 30, 2020.

athe Chinese Office Action dated Jun. 3, 2020 for Chinese Patent Application No. 201680007372.4.

GESE Success, Letters Educational , UK, 2006, p. 19 ( Year : 2006).

The Office Action for the Argentina Patent Application No. 20160101901 Dated: Aug. 19, 2020.

The Brazilian Office Action dated Aug. 8, 2020 for Brazilian Patent Application No. BR112017004017-4.

The Office Action from the Canadian Patent Application No. 2,951,715 dated Aug. 28, 2020.

Labedz et al., Precise Mass Determination of Single Cell With Cantilever-Based Microbiosensor System, PLOS One, http//:doi.otg/10.137/journal.pone.018838, Nov. 21, 2017,pp. 1-14.

The International Search Report and Written Opinion for the Application No. PCT/US20/55174 dated Mar. 18, 2021.

Xu et al., Continuous ethanol production using self-flocculating yeast in a cascade of fermentors' Enzyme and Microbial Technology 37 (2005) 634-640, entire document esp p. 635-636.

https://en.wikipedia.org/windex.php?title=Clean-in-place&oldid=889731953'Clean-inplace'27 Mar. 2019, entire document esp p. 2.

Best way to keep dog food and treats fresh -Vacuum seal!, vacmasterfresh.com, Aug. 26, 2015 [online], [retrieved Feb. 11,

(56)               References Cited

OTHER PUBLICATIONS

2021]. Retrieved from the Internet<https://www.vacmasterfresh.com/fresh-bites-blog/ best-way-to-keep-dog-food-and -treats-fresh-vacuum-seal/>(Year:2015).

The Pelleting Process, California Pellet Mill Co., May 17, 2017[online], [retrieved Feb. 11, 2021]. Retrieved from the Internet<https://www.cpm.net/downloads/ Animal%20Feed%20Pelleting.pdf>(Year:2017).

Vibrating Fluid Bed Dryers, Carrier Vibrating, May 12, 2017[online], [retrieved Feb. 17, 2021].Retrieved from the Internet<https://www.carriervibrating.com/equipment/dryers/vibrating/>(2017).

Imran M. et. al., Role of Enzymes in Animal Nutrition: A Review, PSM Vet. Res., 01(2)(2016): 38-45. (Year: 2016).

How many different chemical reactions ca a single enzyme catalyze?, Truong-Son N, Jan. 3, 2016 [online], [retrieved Mar. 4, 2021]. Retrieved from the Internet<https://socratic.org/questions/jo-many-different-chemical-reactions-can-a single-enzyme-catalyze>(Year:2016).

The International Search Report and Written Opinion for the International Application No. PCT/ US2020/057558 dated Jan. 27, 2021.

The Office Action for the Chinese Application No. 201680007372.4 dated Feb. 22, 2021.

The Office Action for the Brazilian Patent Application No. BR 11 2015 003793-3 Feb. 2, 2021.

The Office Action dated Dec. 4, 2020, for Chinese Patent Application No. 201680003607.2.

The International Preliminary Report dated May 12, 2022 for the International Application No. PCT/US2020/057558.

International Search Report and Written Opinion of the International Search Authority dated Apr. 11, 2022 for International Application No. PCT/US 2022/13332, 16 pages.

International Preliminary Report on Patentability dated Apr. 21, 2022 for International Application No. PCT/US2020/055174, 9 pages.

International Preliminary Report dated May 12, 2022, for the International Application No. PCT/US2020/057558.

The First Office Action dated Dec. 26, 2022 from Chinese Patent Application No. 202080073152.8.

The First Office Action dated Jan. 10, 2023 from Chinese Patent Application No. 202080073152.8.

* cited by examiner

Corn Kernel

Hull

Floury Endosperm

Horny Endosperm (cells filled with starch granules in a protein matrix)

Germ

Tip Cap

Bunge Website numbers
Yellow Dent corn
Table 1     Dry basis

| | % on Kernel | Starch | Protein | Oil | Ash | Sugars | Fiber |
|---|---|---|---|---|---|---|---|
| Endosperm | 82.90% | 88.40% | 8% | 0.80% | 0.30% | 0.60% | 1.90% |
| Germ | 11% | 11.90% | 18.40% | 29.60% | 10.50% | 10.80% | 18.80% |
| Pericarp | 5.30% | 7.30% | 3.70% | 1% | 0.80% | 0.30% | 86.90% |
| Tip Cap | 0.80% | 5.30% | 9.10% | 3.80% | 1.60% | 1.60% | 78.60% |
| Whole kernel | 100.00% | 75% | 8.90% | 4% | 1.50% | 1.70% | 8.90% |
| wt. in Lb./Bu | 47 | 35.25 | 4.183 | 1.88 | 0.705 | 0.799 | 4.183 |
| Endosperm | 38.963 | 34.44329 | 3.11704 | 0.311704 | 0.116889 | 0.233778 | 0.740297 |
| Germ | 5.17 | 0.61523 | 0.95128 | 1.53032 | 0.54285 | 0.55836 | 0.97196 |
| Pericarp | 2.491 | 0.181843 | 0.092167 | 0.02491 | 0.019928 | 0.007473 | 2.164679 |
| Tip Cap | 0.376 | 0.019928 | 0.034216 | 0.014288 | 0.006016 | 0.006016 | 0.295536 |
| pericap+tipcap | 2.867 | 0.201771 | 0.126383 | 0.039198 | 0.025944 | 0.013489 | 2.460215 |
| % comp | 100.00% | 7.04% | 4.41% | 1.37% | 0.90% | 0.47% | 85.81% |
| Total wt in lb. | 49.867 | 35.46206 | 4.321086 | 1.92042 | 0.711627 | 0.819116 | 6.632687 |

Fig. 13

METHODS OF AND SYSTEMS FOR A DRY MILLING PROCESS WITH TWO STEPS LIQUEFICATIONS

CROSS-REFERENCE TO RELATED APPLICATION(S)

This application claims priority under 35 U.S.C. § 119(e) of the U.S. Provisional Patent Application Ser. No. 63/315, 431, filed Mar. 1, 2022 and titled, "METHODS OF AND SYSTEMS FOR A DRY MILLING PROCESS WITH TWO STEPS LIQUEFICATIONS," which is hereby incorporated by reference in their entirety for all purposes.

FIELD OF THE INVENTION

The present invention relates to a dry milling process. Specifically, the present invention relates to a dry milling process with multiple liquefication stages.

BACKGROUND OF THE INVENTION

The background description provided herein is for the purpose of generally presenting the context of the present disclosure. Work of the presently named inventors, to the extent the work is described in the present disclosure, as well as aspects of the description that may not otherwise qualify as prior art at the time of filing, are neither expressly nor impliedly admitted as prior art.

Most of the raw materials of dry mill processes for alcohol production are corns and some are rice and wheat. In a corn anatomy, the floury endosperm is loosely packed starch granules that are very easy to be liquefied. The horny endosperm (common call grit) is a cell that fills with starch granules in protein matrix, which is very hard to be liquefied because it is protected by protein cell wall. The germ is a cell that fills with oil in protein matrix with inorganic salt inside. The pericarp (commonly referred to as hull) and tip cap are cellulose type materials, which serve as a waterproof protect layer.

Table 1 (FIG. 13) illustrates compositions of a corn. One bushel of corn has 49.87 lb. dry material, which contains 35.46 lb. of starch and 1.92 lb. of oil. If all the starch is converted to alcohol, 3 gal/bushel alcohol yield should be obtained. However, a typical dry mill plant has about 2.8 to 2.9 gal alcohol yield/Bu. The oil yield of typical dry mill plants ranges from 0.5 to 0.9 lb./Bu. Typical oil recovery system only recovers less than 50% of oil inside the corn. The total solid in a whole stillage is 15 lb. to 16 lb./Bu, which contains more than 1 lb./Bu germ particles, because germ particles are rubber type material and are very hard to break up in a hammer mill even when the corn is ground to 2 to 3 mm size.

A process 100 of FIG. 1 illustrates a typical corn dry mill for fuel alcohol production. The corns are fed to a hammer mill at Step 101 with a screen size of #6 to #8 (%₆₄ inch open size) to form corn flour with particle sizes between 50 microns to around 3 mm. Corn flour is mixed with cook water and a backset stream from a backend (e.g., after fermentation) to a slurry tank at a Step 102 to liquefy the starch by GA enzyme at a temperature of 190 to 200 F. The high-pressure stream jet cooker is normally added to slurry tank to speed up the liquefication step. This slurry mass is fed to a liquefication step at a Step 103 for 2 to 3 hour holding time, which gives time for GA enzyme to attack starch inside germs and grits that are protected by protein matric cell wall. Pure starch slurry can complete the liquefication to form a very low viscosity liquid in one hour holding time in a wet mill process. However, 2 to 3 hour holding time in a dry mill process is still not enough based on prior data.

The mash from liquefication tank at the Step 103 goes through heat exchanger to cool off and is sent to fermenters at a Step 104. In the fermenter at the Step 104, the liquefied starch is converted to glucose then to alcohol by a simultaneous saccharification and fermentation. This simultaneous step is referred to in the industry as "Simultaneous Saccharification and Fermentation" (SSF). The beer from the fermenter is sent to a distillation column to boil off the alcohol at a Step 105. The whole stillage from bottom of the distillation column is sent to a whole stillage solid/liquid separation centrifuge (decanter) at a Step 106 to separate the solid (DDG) from liquid (thin stillage). The DDG contains mainly the coarse solid (e.g., hull, tip cap, grit and germ particle) and some find solids (e.g., fine fiber and corn protein etc.). The thin stillage contains mainly all soluble solid and corn oil plus fine solid (e.g., spent yeast cell and germ/corn protein etc.). The thin stillage from a decanter centrifuge as an overflow stream is sent to an evaporator at a Step 107 to boil off water and to be concentrated to about 35% of DS (dry material) syrup. The syrup contains about 2% of oil is sent to an oil recovery centrifuge at a Step 108 for recovering valuable byproduct including corn oil. At a DDGS rotary dryer of a Step 109, the de-oil syrup from the oil recovery centrifuge at a Step 108 is mixed with a wet cake (DDG) from a decanter centrifuge at a Step 106 to produce another byproduct (DDGS). The DDGS contains about 30% of protein, 8% of oil and more than 4% bond starch, because more than half of germs are still not broken up in a hammer mill.

In FIG. 2, a process 200 using a front wet milling process, as described in the U.S. Pat. No. 9,012,191, has been provided to break up germ and grit particles to increase alcohol yield up to 3% and oil yield up to 30% (from 0.4 to 0.7 lb.//Bu) by adding a liquid/solid separation at a Step 201 and wet milling at a Step 202 to typical dry mill systems. The solid/liquid separation at the Step 201 separates liquefied starch solution from the solids (grit and germ particle). The wet cake from solid/liquid at the Step 201 is sent to the wet milling at the Step 202 to break up smaller particles, so that the starch and oil can be released from the protein matrix cell wall. One section of the paddle screen is used at the solid/liquid separation at the Step 201 and grind mill is used at the wet milling at the Step 201.

In FIG. 3, a process 300 provides a multi-stage solid/liquid separation step and a wet grind step with counter current washing system, which has been developed to produce pure fiber before a fermenter. The process 300 is provided in the U.S. Pat. Nos. 9,689,003, 9,718,006 and 9,732,302. The pure fiber still contains 20% of protein, 7% of oil, and 2.5% of bond starch and more than 2% of liquefied starch. The process 300 as shown in the FIG. 3 is a multistage (only 2 stage counter current set up). Two solid/liquid separation at Steps 201 and 302 and two wet milling at Steps 202 and 303 are added to typical dry mill system to increase alcohol and oil yield. The process 300 produces pure fiber without going through the fermentation at the Step 104.

In a FIG. 4, the coarse fiber DDG (pericarp and tip cap) can be separated out before fermentation at the Step 104, which increases a fermentation capacity about 10%, increase fermentation and increase heat exchange efficiency as well. Three stage solid/liquid separations at Step 101, 201, and 302 use back set and cooking water to do counter current washing the fiber to separate and produce pure fiber as feedstock for a secondary alcohol production or for paper industry as shown in a Process 400 in the FIG. 4. Two stages of wet milling at the Steps 202 and 303 are also added to the typical dry mill system. More stage solid/liquid separation and wet milling stage can be added to the process if the benefits can justify the equipment investment. Up to five stage counter current setup has been used in commercial scale, but the pure fiber still contains more than 20% of protein, more than 5% of oil, and more than 2.5% of bond starch with more than 1% of liquefied starch.

SUMMARY OF THE INVENTION

The present disclosure provides a two-step liquefication (e.g., using high and low Be liquid media) process in a dry milling process/plant. In the two-step liquefication process, the starch in the floury endosperm of a corn feedstock is liquefied in a high Be liquefication tank, which is subsequently sent to a fermenter for producing alcohol. Further, the starch in horny endosperm (e.g., the cells fill with starch granules in protein matric) and the oil/starch in germ (e.g., the cell fill with oil in protein matric) are further liquefied in a low Be liquification tank for longer soaking and cooking time, wherein the low Be liquification tank is used to soften grit and germ particles. After the low Be liquification process, the content is sent to a wet grinding step to be broken up and release starch and oil.

A novel design of a three/four section paddle screen with a high-rate replacement washing capability in this disclosure is used to wash off liquefied starch and produce pure fiber (pericarp and tip cap) before fermentation. With this two-step liquefication steps, more starch is liquefied (e.g., for producing more alcohol) and more oil is released (e.g., for producing more value corn oil and germ protein byprod-ucts). Related U.S. Pat. No. 11,166,478 is incorporated by reference for all purposes.

The above-mentioned two-steps liquefication process (e.g., two stages liquefication process) soaks/cooks the germ/grit particles for over two hours, which soften or make the particles easy to break into smaller particles by using a solid ring design (U.S. Pat. No. 9,352,326, which is incorporated by references for all purposes), which can use a grind mill in a wet milling step. The two or three solid/liquid separating step with a high-rate displacement washing in three/four sectional new patented paddle screen can be used to separate fiber from protein and liquefied starch, which produces pure fiber with less than 15% of protein, less than 5% of oil, less than 2% of bond starch, and less than 1% of liquefied starch. This pure fiber can be used to make DDG (as animal feed), which can bypass/skip the process of fermenting to increase fermenter capacity and efficiency. The pure fiber can be used as a feedstock for secondary alcohol production or paper industry.

In addition, a new power saving highly efficient nozzle centrifuge is used, which is followed by using a high efficiency protein decanter to produce high value yeast/germ protein cake with an extra clean content (e.g., less than 2% by volume of spin solid). The thin stillage uses a new process by recycling an overflow stream from a protein decanter to a nozzle centrifuge. This extra clean thin stillage can be evaporated to have an 85% DS syrup by using a vacuum force recycle evaporator in conjunction with waste heat recovering system to save energy. This highly concentrated syrup with 85% of DS can bypass the dryer and can be added to a dry feed to form a highly nutrient animal feed. The portion of syrup can also be used at an enriching step, which converts residual sugar to lactic acid with up to 20% of DB (in dry base). The conversion of the sugar to lactic acid can be done by adding a mixture of probiotic culture in a secondary fermentation step, which produces up to $10^{\wedge 9}$ CFU probiotic per unit syrup. This enriched probiotic syrup can act as a bonding agent to form a new enrich probiotic pellet/tub animal feed (Related U.S. Pat. No. 11,166,478 is incorporated by reference for all purposes).

BRIEF DESCRIPTION OF THE DRAWINGS

The accompanying drawings, which are incorporated in and constitute a part of this specification, illustrate embodiments of the invention and, with a detailed description of the embodiments given below, serve to explain the principles of the invention. They are not intended to limit the scope of the invention.

FIG. 13 illustrates composition of a corn.

DETAILED DESCRIPTION OF PREFERRED EMBODIMENTS

Reference is made in detail to the embodiments of the present invention, examples of which are illustrated in the accompanying drawings. While the invention is described in conjunction with the embodiments below, it is understood that they are not intended to limit the invention to these embodiments and examples. On the contrary, the invention is intended to cover alternatives, modifications and equivalents, which can be included within the spirit and scope of the invention as defined by the appended claims. Furthermore, in the following detailed description of the present invention, numerous specific details are set forth in order to more fully illustrate the present invention. However, it is apparent to one of ordinary skill in the prior art having the benefit of this disclosure that the present invention can be practiced without these specific details. In other instances, well-known methods and procedures, components and processes have not been described in detail so as not to unnecessarily obscure aspects of the present invention. It is, of course, appreciated that in the development of any such actual implementation, numerous implementation-specific decisions must be made in order to achieve the developer's specific goals, such as compliance with application and business related constraints, and that these specific goals vary from one implementation to another and from one developer to another. Moreover, it is appreciated that such a development effort can be complex and time-consuming, but is nevertheless a routine undertaking of engineering for those of ordinary skill in the art having the benefit of this disclosure.

Virtually all of the fuel ethanol in the United States is produced from a wet mill process or a dry grinding ethanol process. Although generally any type and quality of grain can be used to produce ethanol, a type of feedstock for these processes may use a corn known as "No. 2 Yellow Dent Corn." The "No. 2" refers to a quality of corn having certain characteristics as defined by the National Grain Inspection Association, as is known in the art. "Yellow Dent" refers to a specific type of corn as is known in the art. Sorghum grain is also utilized to a very small extent. Generally speaking, the typical industrial average of ethanol yield for both dry grind and wet mill plants is approximately 10.2 liters (approximately 2.8 gal) of ethanol produced per 25.4 kg (one (1) bushel) of No. 2 Yellow Dent Corn.

Figure 1:
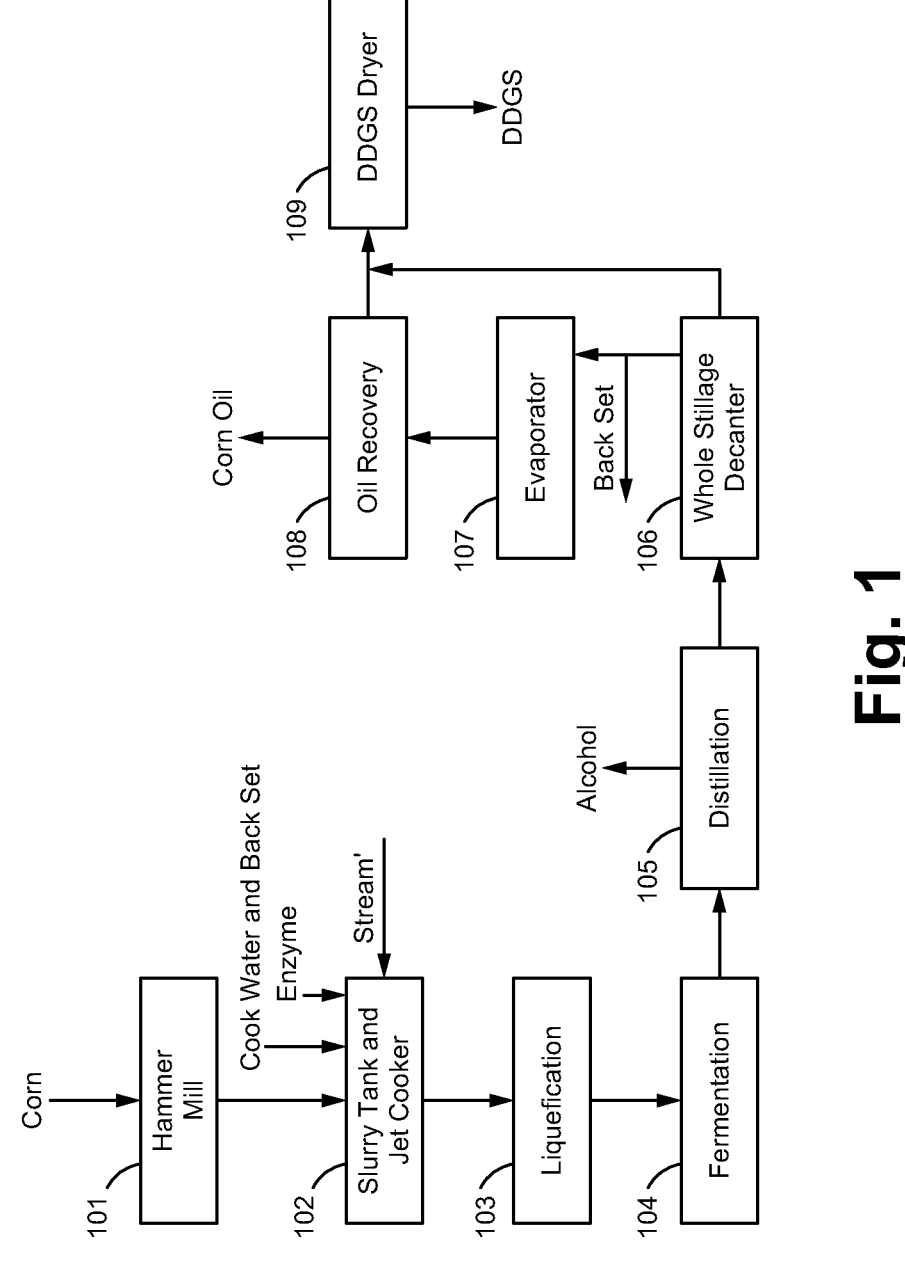
FIG. 1 illustrates a typical dry milling process.
Figure 2:
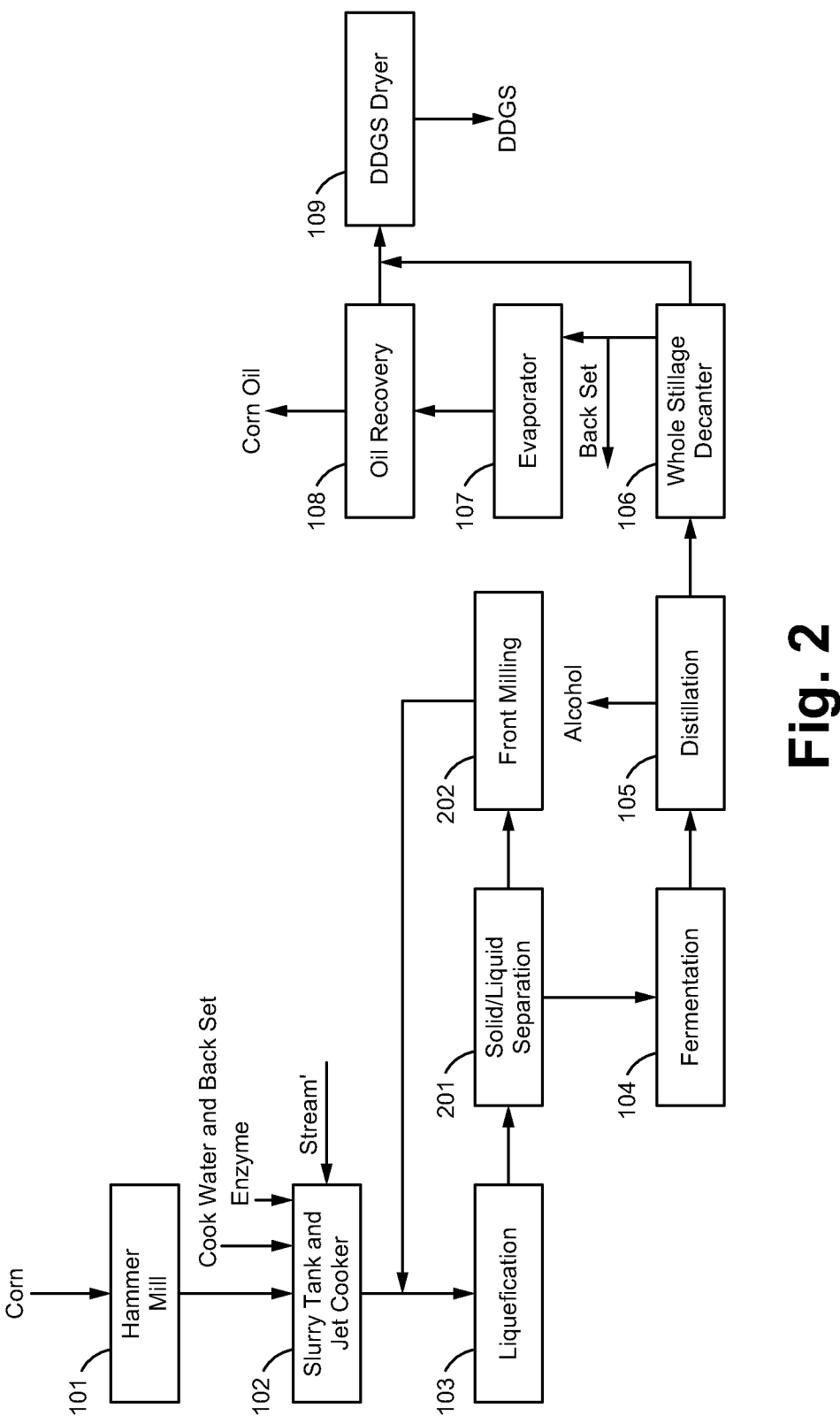
FIG. 2 illustrates a typical dry milling process with a front milling step.
Figure 3:
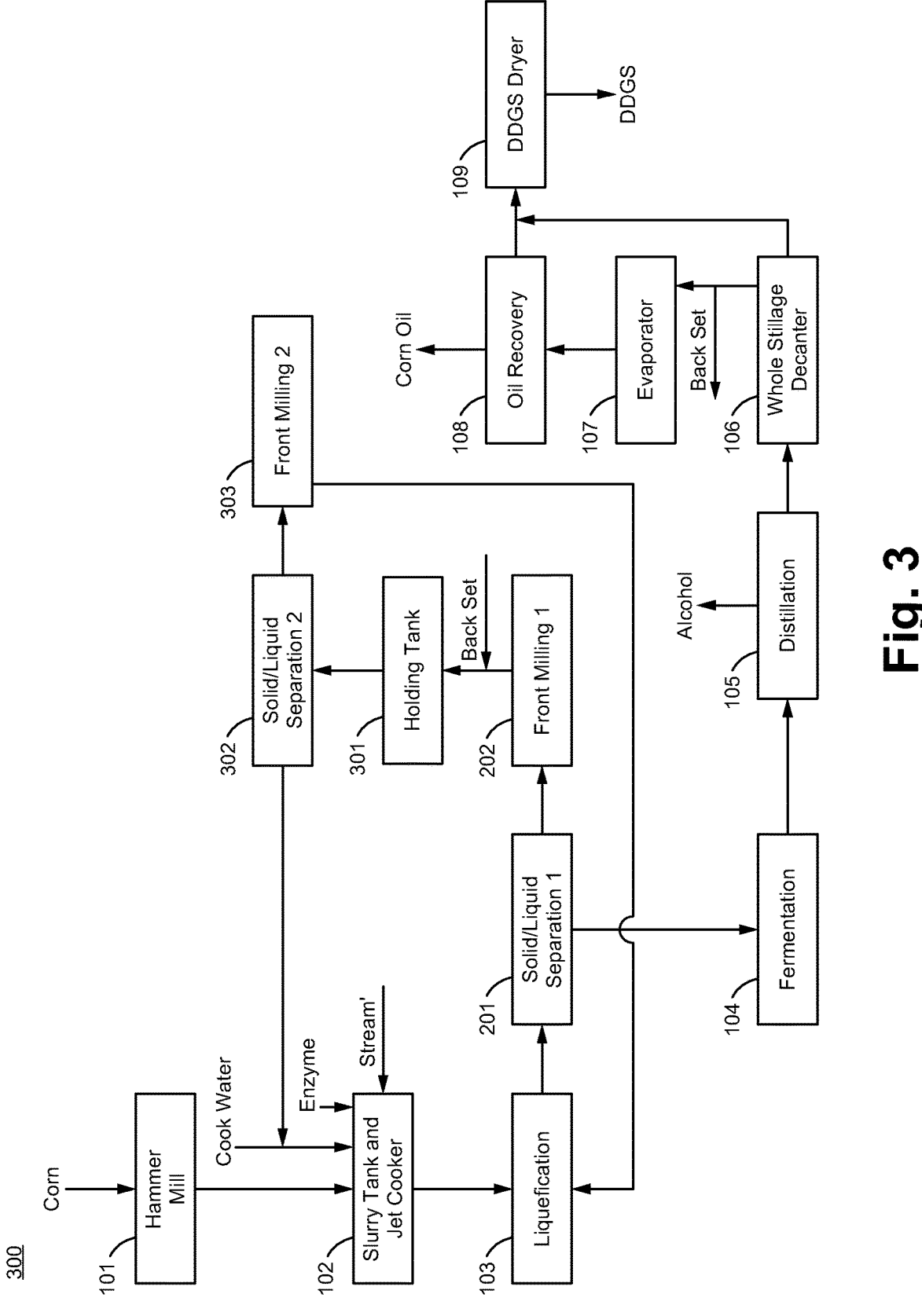
FIG. 3 illustrates a typical dry milling process with multi-milling stage and multi-solid/liquid separation stage with a counter current dilution washing setup.
Figure 4:
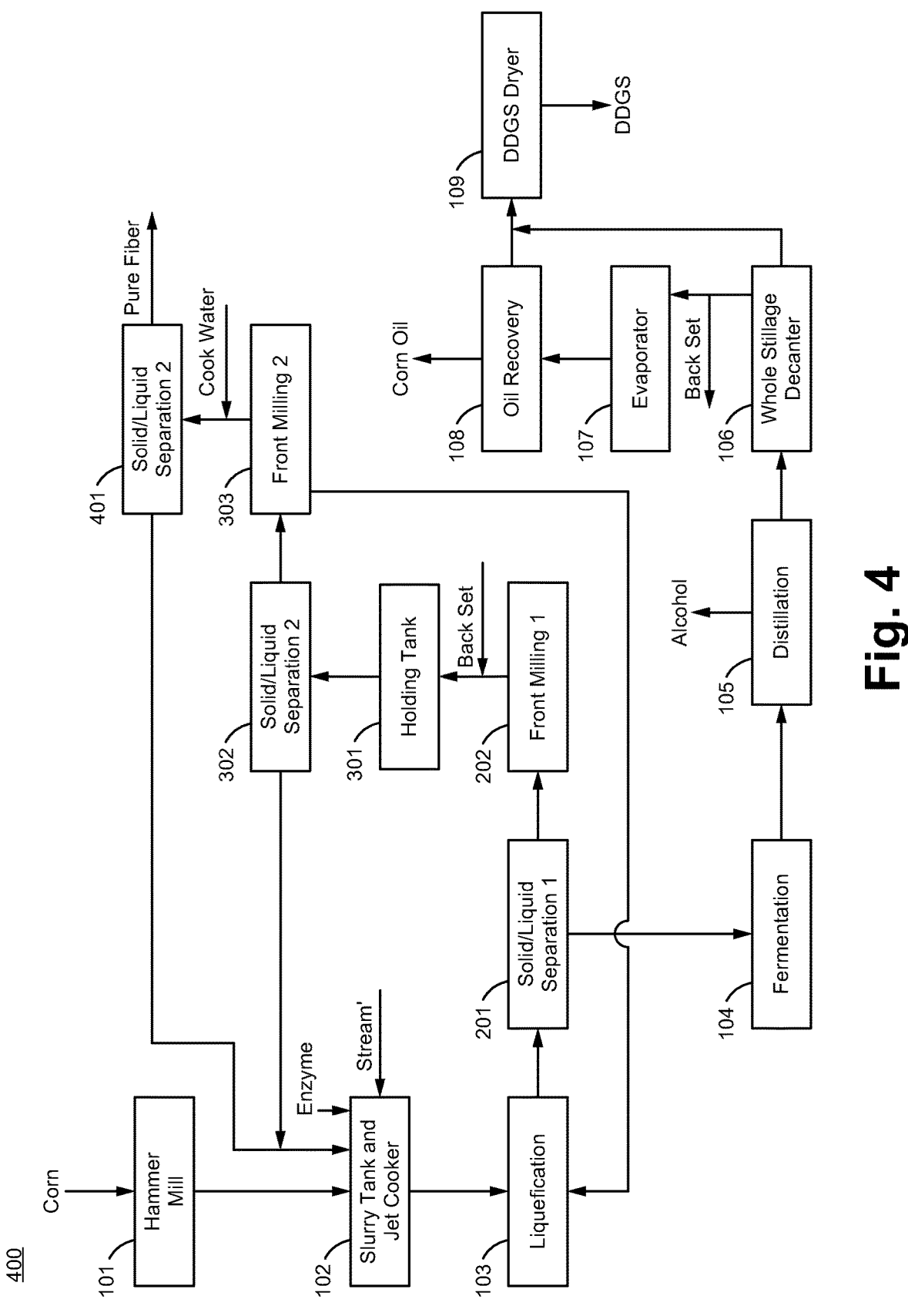
FIG. 4 illustrates a typical dry milling process with multi-milling stage and multi-solid/liquid separation stage with counter current dilution washing to produce pure fiber before fermentation.

With respect to the dry milling process, the Process 100 of the FIG. 1 is a schematic flow diagram of a typical dry grinding ethanol production. The part of the process 100 that occurs prior to distillation and dehydration at a Step 105 is referred to as the "front-end", and the part of process 100 that occurs after distillation and dehydration at the Step 105 (hereinafter "dehydration") may be referred to as the "back-end". In some embodiments, the fermentation at the Step 104 is used as a point to distinguish the front-end and back-end processes.

The frontend of process 100 begins with a grinding step at a Step 101, in which dried whole corn kernels are passed through hammer mills for grinding into corn flour. The screen openings in the hammer mills typically are of a size 7/64, or about 2.78 mm. The resulting particle distribution typically yields a very widespread, bell type curve, which includes particle sizes as small as 45 microns and as large as 2 to 3 mm.

Grinding at the Step 101 is followed by a series of liquefaction Step 103, wherein ground corn flour is mixed with cook water to create a slurry in a slurry tank at a Step 102. An enzyme such as alpha-amylase is typically added, followed by an optional jet cooker step (not shown) to the liquefied starch at higher temperatures. If needed, the pH is adjusted here to about 5.0 to 6 and the temperature maintained between about 50° C. to 105° C. to convert the insoluble starch in the slurry to soluble starch. Typical dry mill plant has about 2 to 3 hour holding time in liquefaction tank. The stream after the liquefaction at a Step 103 has about 26 to 38% dry solids (DS) content with all the components contained in the corn kernels, including sugars, protein, fiber, starch, germ, grit, and oil and salts, for example. There generally are three types of insoluble solid particles in the liquefaction stream: fiber, germ, and grit, with all three solids having about the same particle size distribution. About 25 to 35% solid volume is in the mash. Those grit and germ particles contain starch and oil will end up in byproduct DDGS in back-end whole stillage separation at the Steps (106, 107, 108, and 109) and result in lower alcohol and oil yield.

Figure 5:
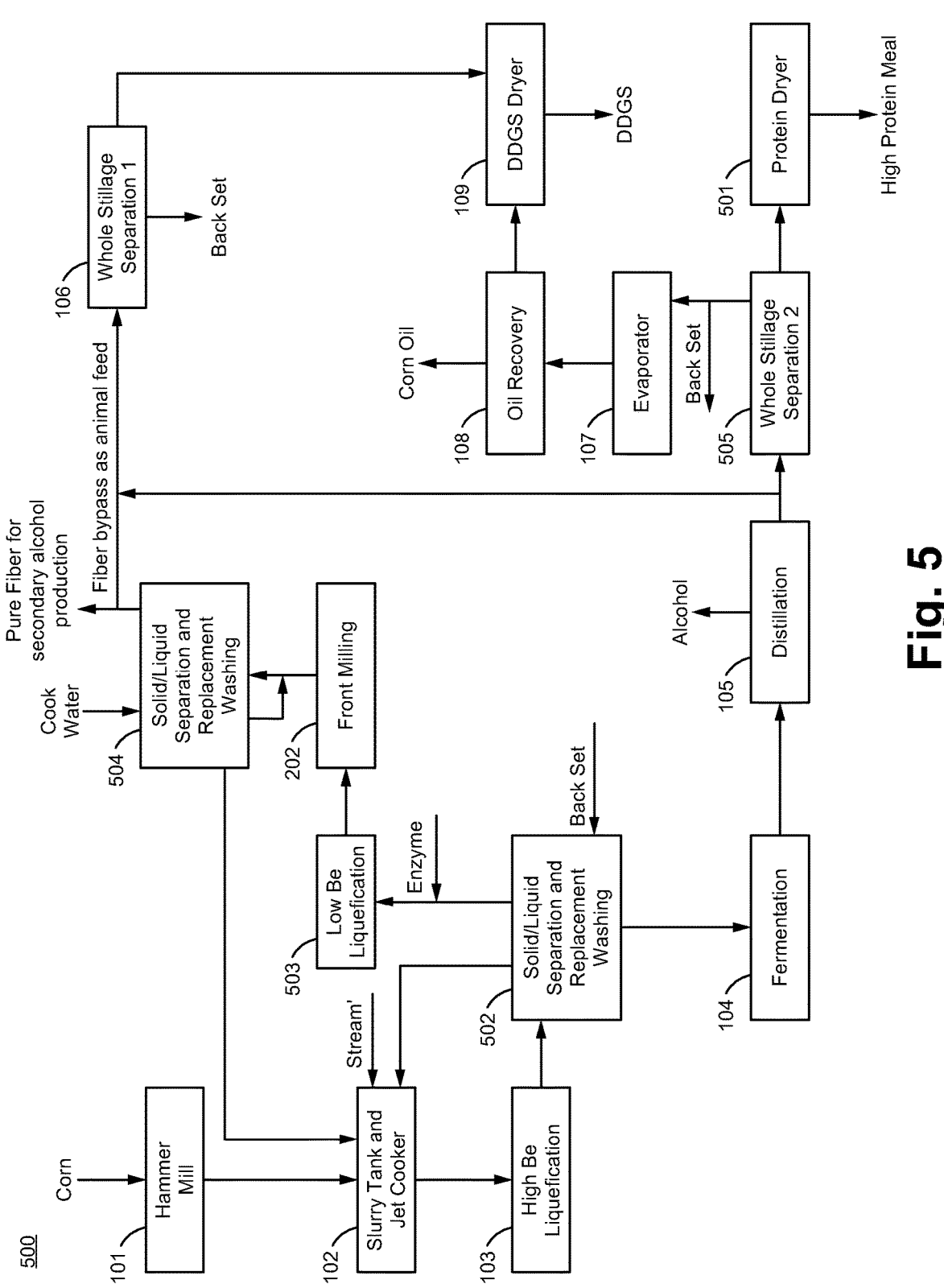
FIG. 5 illustrates a two-stage liquefication process with fiber bypass and one protein feed with two solid/liquid separating steps in accordance with some embodiments.
Figure 5A:
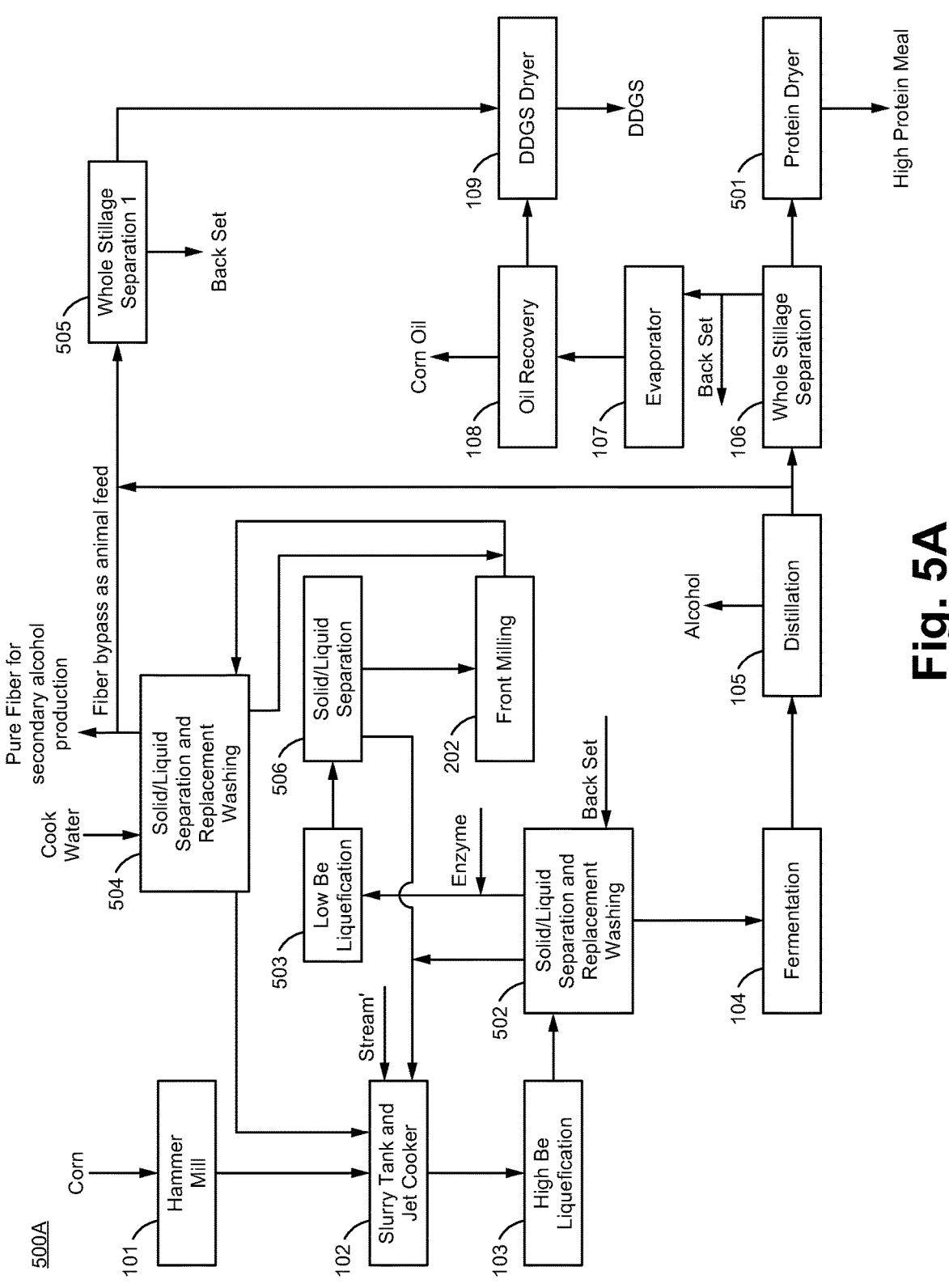
FIG. 5A illustrates a two-stage liquefication process for pure fiber and one protein feed with three solid/liquid separating steps in accordance with some embodiments.

FIG. 5 illustrates a process 500 having two-stage liquefication process with fiber bypass and one protein feed with two solid/liquid separating steps in accordance with some embodiments.

At a Step 101, the corns are milled at a hammer mill. At a Step 102, the milled content is sent to a slurry tank and a jet cooker.

At a Step 103, germ and grit particles are separated from mash using a high Be solution (around 23 Be) (e.g., one Be=1.77% dry material) in a liquefication tank. A high Be solution can be in a range of from 20-27 or higher than 20 Be. The content at the Step 103 is sent to a solid/liquid separation at a Step 502.

At the Step 502, three, four, or more section screens are used with a high-rate replacement washing design, which is able to be a paddle screen design.

At a Step 503, the wet cake (containing fiber, germs, and grit particles) from the paddle screen of the Step 502 is soaked and cooked in a low Be (less than 5 Be) liquefication tank. Still at the Step 503, the back set stream is used as washing water to do displacement washing inside this paddle screen from more than 23 Be liquefied starch to be a less than 5 Be liquefication solution in the low Be liquefication tank.

At a Step 202, the germ and grit particles are soaked/cooked for more than two hours with the addition of fresh GA enzyme plus optional other enzymes, such as cellulase and protease. In some embodiments, cell wall degrading enzymes are used to soft/degrade the protein cell wall to release starch and oil at the wet milling.

At a Step 504, the germ and grit particles are much easier to be broken up after soaking/cooking in the low Be liquefication tank. Still at the Step 504, the wet milling solid contains broken germ and grit particles and coarse fiber (e.g., hull and tip cap), which are sent to other 3 or 4 sectional paddle screen with a high-rate displacement design. The 3 or 4 sectional paddle screen separates broken germ and grit fine particles from the coarse fiber by using particle size and shape difference. The cook water is used as washing water in this paddle screen washing off small germ and grit particles and liquefied starch to produce pure fiber as feedstock for secondary alcohol production or paper industry.

At a Step 106, the pure fiber also can be mixed with a portion (around 23% of the total flow) of a whole stillage, which can be fed to one or two whole stillage decanters at the Step 106 to remove excess water and produce wet cakes (DDG).

At a Step 109, the content from the Step 106 is mixed with the de-oil syrup from an oil recovery step at a Step 108 using a DDGS dryer to produce dry DDGS cow feed. The liquid from the whole stillage decanter at the Step 106 is recycled as backset stream to avoid any liquefied starch loss in the fiber bypass.

FIGS. 1-4 illustrate backend processes in dry mill plants. In general, the whole stillage is normally fed to a multi-unit decanter to separate insoluble solid (e.g., wet cake mainly having fiber, germ, grit and some protein and fine fiber) and liquid (e.g., thin stillage) containing 6 to 8% total solid and 4 to 6% soluble solid. A portion of this liquid (about 23% of the flow) is used as back set, which is recycled back to front end as a backset stream to save energy.

FIG. 5 illustrates a process 500 in accordance with some embodiments. The back-end process (e.g., after fermentation) in this disclosure is further improved. The multi whole stillage decanter in the whole stillage solid/liquid separation is divided into two groups. About ¼ of the units are used as DDG dewater device at the Step 106. The rest of the units are used as a corn protein separation/dewatering device at a Step 505.

Referring to FIG. 5 at the distillation at a Step 105, the whole stillage flow is split to two streams. One of the two streams goes to the Step 106 and the other stream goes to the Step 505. The flow rate to the whole stillage separation at the Step 106 is controlled to ensure the overflow from the decanter at the Step 106 is the amount of backset flow as needed. The liquid (e.g., overflow) from the Step 106 is used as a backset, and the liquid from the Step 505 is a thin stillage, which is sent to an evaporator at a Step 107. The cake from the Step 106 is used as DDG with about 30% parfait for cow feed. The cake from the Step 505 is used as corn protein with about 50% protein, which is used as chicken feed.

The thin stillage from the Step 505 enters evaporators in an evaporation at a Step 107 to boil away water, leaving a thick syrup that contains the soluble (dissolved), fine suspended mainly yeast protein.

The concentrated syrup with about 30% DS is fed to an oil recovery at Step 108, where the syrup can be centrifuged to separate oil from the aqueous syrup. The oil can be sold as a separate high value byproduct. The oil yield is normally about 0.4 lb./bu in a typical dry mill plant. This oil yield recovers only about ¼ of the oil in the corn.

Referring to the FIG. 5 at the Step 105, around one-half of the oil inside the corn kernel remains inside the germ after the distillation, which cannot be separated in a typical dry grind process.

Nonetheless the improved Process 500 of FIG. 5 is a system with two liquefication stages (e.g., Steps 103 and 503) and two solid/liquid separation and replacement washing steps (e.g., Steps 502 and 504) plus a wet milling step (e.g., the Step 202), which break the germ and grit particles, so that more oil and starch are released resulting in increased alcohol yield up to 3% and the increased oil yield up to 1.4 lb./bu. The process 500 is able to recover about 75% of oil inside the corn. Further, the process 500 of FIG. 5 produces pure fiber having a yield of about 3 lb./bu. with less than 15% protein, less than 5% of oil, and less than 3% of starch and sugar. The system of the process 500 also produces about 3 to 5 lb./Bu high protein animal feed with 50% protein and about 8 to 10 lb./bu DDGS with 30% profat (about 25% protein and 5% oil), which is suitable to be used as cow feed.

Still referring to FIG. 5, the device for wet milling step 202 can be a Supraton, a roller mill, a pin mill, or a grind mill. The device for performing fiber dewatering at the Step 505 can be a screen bowl decanter, a typical decanter, a screw press, or a roller press among other dewatering devices.

Still referring to FIG. 5, the device for solid/liquid separation and replacement washing at the Steps 502, 504 and 506 is a novel four sectional paddle screen, which is an improved design from the three-section paddle screen (e.g., U.S. Pat. No. 11,166,478, which is incorporated by reference for all purposes).

Figure 11:
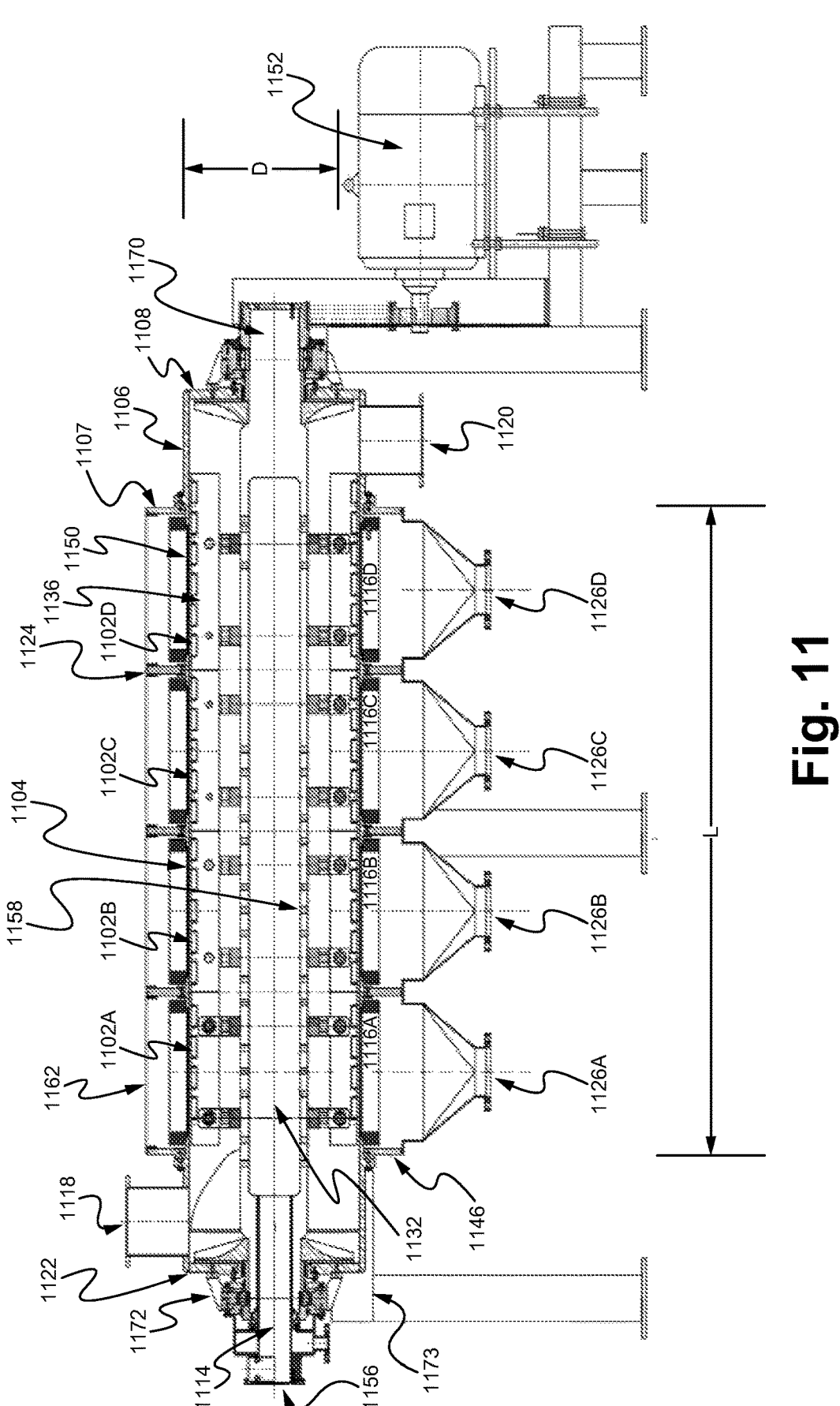
FIG. 11 illustrates a cross sectional view of a four-section paddle screen 1100 in accordance with some embodiments.
Figure 12:
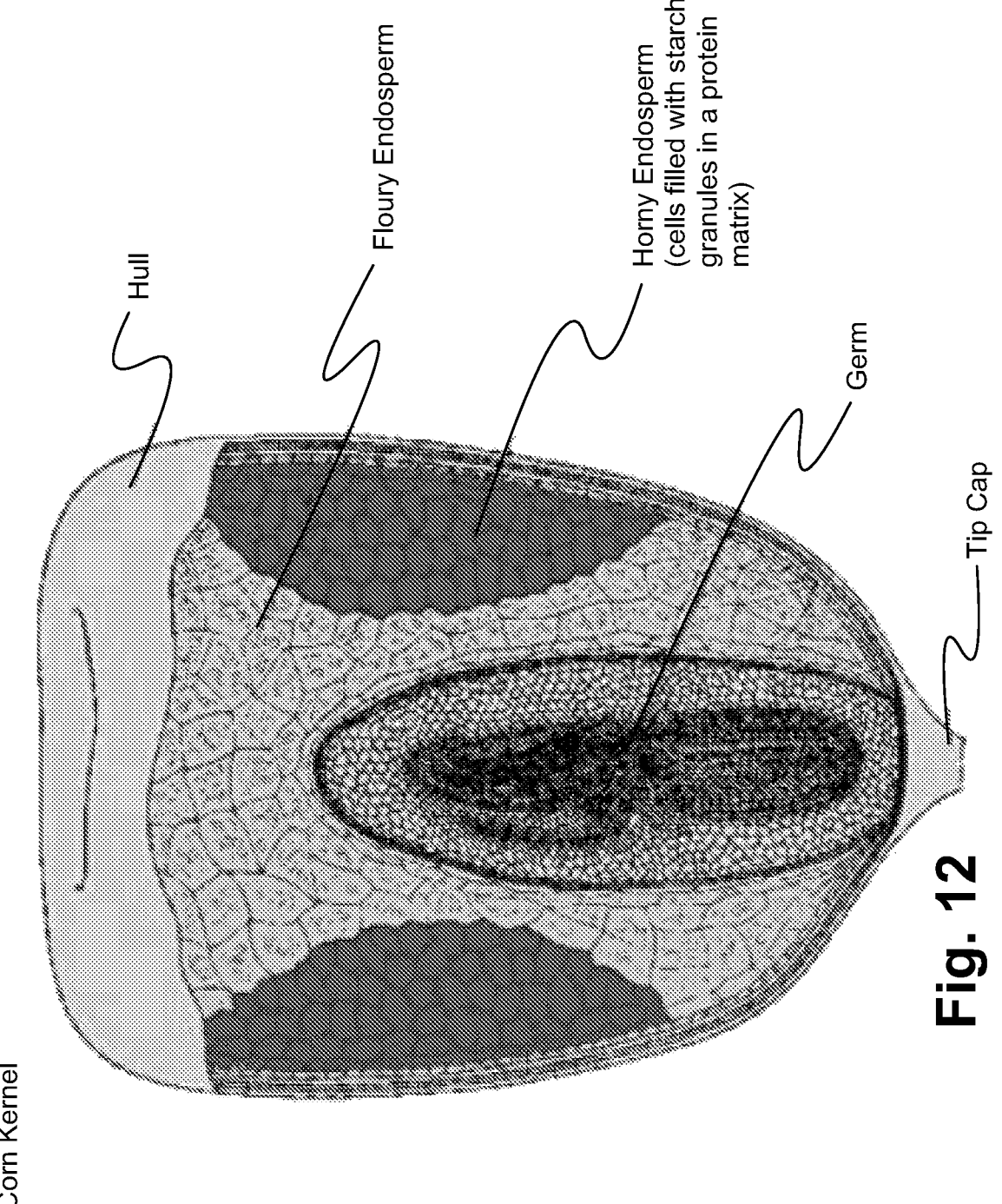
FIG. 12 illustrates a cross sectional view of a corn.

FIG. 11 illustrates a four section paddle screen 1100 in accordance with some embodiments. The Apparatus 1100 is a single, self-contained device configured for solid/liquid separating and high-rate replacement washing on solid, e.g., filtering, a material (e.g., fiber) from a liquid medium, then further washing/de-watering the material. The apparatus 1100 can perform both the initial filtering of the slurry and replacement washing of the fiber to clean the fiber and to remove starch/protein/oil that is associated with the fiber, as well as washing/dewatering of the fiber.

Still referring to FIG. 11, the novel four section paddle screen for the Step 502 uses a CL model. The first two section screen/chamber is used for solid/liquid separation. The last two section screen/chamber are used for replacement washing and dewater. The novel four section paddle screen for the Step 504 uses WH model. The first section screen/chamber is for solid/liquid separation. The $2^{nd}$ and $3^{rd}$ section screen/chamber are for replacement washing. The $4^{th}$ section screen is used for dewatering function. The new four section paddle screen for the Step 506 uses DW model. The first section screen/chamber is for solid/liquid separation. The $2^{nd}$, and $3^{rd}$, and $4^{th}$ section screen/chamber are for dewatering function. Throughout the present Disclosure, similar referencing numbers refer to same or similar function of the respective steps. For example, Step 502 in FIGS. 5, 5A, 6, 7, 9 refers to similar or same function disclosed herein.

Still referring to the FIG. 11, the apparatus 1100 includes a stationary, cylindrically shaped screen container 1102, formed with four sections, 1106A, 1106B, 1106C and 1106D in accordance with some embodiments. Screen 1102 has a plurality of screen slot openings 1104 formed therein to permit the liquid medium, including any wash water and any small germ/grit particle and/or fine suspended particles (including yeast from fermentation) off the fiber, for example, to pass through the screen 1102, while preventing the coarser fiber from passing through. Screen 1102 is disposed in an interior of a housing 1106, which includes a first end housing 1107, and an end wall 1108. The screen 1102 is situated about a central axis 1114 of apparatus 1100 and extends substantially along the length (L) thereof.

Although a single or a unitary screen is able to be utilized here, screen 1102 is shown having individual first, second, third, and fourth screen sections 1102A, 1102B 1102C and 1102D, which generally correspond respectively to the lengths of first, second, third, and four zones 1116A, 1116B, 1116C, and 1116D of the housing 1106.

First screen section 1102A is situated approximately to a tangential feed inlet 1118 located at one end of apparatus 1100 adjacent to a first zone 1116A to receive the incoming liquid medium containing a quantity of material to be separated and extends partly along about ¼ the length (L) of apparatus 1100.

Second screen section 1102B is situated adjacent and downstream from first screen section 1102A. Third section screen 1102C is situated adjacent to and downstream from second screen section 1102B. Fourth section screen 1102D is situated adjacent to and downstream from third screen section 1102C and extends partly along the remainder of the length (L) of apparatus 1100 to the location of a wet solid discharge chute 1120, which is situated at a downstream end of apparatus 1100, adjacent four zone 1116A, 1116B, 1116C and 1116D.

It is noted that the lengths of first, second and third screen sections 1102A, 1102B, 1102C and 1102D are variable in different embodiments. Also, while only four screen sections 1102A, 1102B, 1102C and 1102D are shown here, it is understood that more than four screen sections are utilized in different embodiments. In addition, while the diameter of the screen 1102 is shown as being substantially constant along its length, the screen diameter is variable along at least one or more portions thereof.

Screen 1102 is able to be formed as a wedge wire type, with slot openings vertical or parallel or at any angle to liquid flow direction, or a round hole, thin plate screen. In other embodiments, the screen is able to be a bar screen, a thin metal screen (e.g., mesh screen), or a filter cloth having a metal reinforced design. Those of ordinary skill in the art will recognize other types of screens that are used in accordance with embodiments.

Screen openings 1104 are varied depending on the specific application and on the type of material being filtered. For example, for fiber filtration, it is contemplated that openings 1104 in first, second, third, and fourth screen sections 1102A, 1102B, 1102C and 1102D are sized from about 50 microns to about 1 mm. In another embodiment, openings 1104 are from about 50 microns to about 500 microns.

Openings 1104 in first screen section 1102A can be the same size as the openings in second screen section 1102B, larger than the openings in second screen section 1102B, or smaller than the openings in second screen section 1102B. Those of ordinary skill in the art will recognize how to determine the size of the openings 1104 to achieve the filtration of the predtermined material. Selecting the right type of screen, screen opening size, and slot opening vertical or parallel to flow or round hole can select for those screens to meet any process need.

As indicated above, housing 1106 generally surrounds screen 1102 and is adapted to collect the medium that passes through openings 1104 in screen 1102. The housing 1106 includes two side walls 1107 and three internal panel to divide four zones 1116A, 1116B, 1116C and 1116D so as to define the interior. Housing 1106 further includes three interior panels 1124 that compartmentalizes housing 1106 into first, second, third and fourth zones 1116A, 1116B 1116C and 1116D, which include first, second, third and fourth hoppers 1126A, 1126B, 1126C and 1126D, respectively, with corresponding outlets for removing the filtered liquid medium and directing the filtered liquid medium to a desired location. First zone 1116A can generally define an initial solid/liquid separation zone, and second zone 1116B may generally define a solid particle separation zone, and third zone 1116C may generally define as washing zone and fourth zone 1116D may generally define as dewatering zone.

The end of fourth zone 1116D includes discharge chute 1120, where the separated and washed/de-watered fiber material can be collected for further processing. Although four zones 1116A, 1116B, 1116C and 1116D are illustrated here, those of ordinary skill in the art will appreciate that the number of separation zones 1116A, the number of solid particle separation zones 1116B and the number of washing zones 1116C and number of dewater zones 1116D can be application specific in different embodiments. The housing 106 can have any suitable shape.

Tangential feed inlet 1118 is at the upstream end of the apparatus 1100 adjacent first zone 1116A and in fluid communication with an interior of first screen section 1102A. Feed inlet 1118 supplies the medium and material (e.g., fiber) to apparatus 1100 and can introduce the medium and material in a swirling fashion (tangential entry along outside wall) to start filtering the fiber upon entry into apparatus 1100. The feed inlet open area can be adjusted depending on the feed rate and feed pressure to make sure the feed tangential speed will be as close as possible to the paddle tangential speed to get the best results.

A plurality of spaced apart paddles/vanes 1136 extend in a radial direction away from a shaft 1132 along axis 1114, such that an outer surface of each vane 1136 is situated in spaced relation to first screen section 1102A. The space between adjacent vanes 1136 defines an open cavity and provides a fluid flow passage for the liquid medium (e.g., slurry and/or wash water) during the filtration of the material (e.g., fiber), and can be sized to accommodate the design throughput of the apparatus.

The number of vanes 1136 can range from about 2 to about 10. In another embodiment, the number of vanes 1136 is from about 4 to about 8. In yet another embodiment, the number of vanes 1136 is 8. The thickness of vanes 1136 can range from about ¼ inch to about 2 inches. In another embodiment, the thickness of vanes 1136 can range from about ¼ inch to about ½ inch.

The shape and orientation of vanes 1136 can be changed to adjust the flow of the liquid material and medium and the filtering characteristic of the apparatus 1100. In some embodiments, vanes 1136 can be oriented in a helical fashion about the length of first section 1116A of shaft 1132. In some embodiments, the pitch or angle of vanes 1136 relative to shaft 1132 is adjustable, as well as the spacing between vanes 1136, which can be constant or variable from one vane 1136 to the next.

Straight vanes, without helical features can be referred to herein as paddles. Each paddle 1136 is connected to shaft 1132 via a plurality of spaced apart support arms 1146. The length of each paddle 1136 can be adjusted. The number of paddles 1136 can range from about 2 to about 10. In another embodiment, the number of paddles 1136 is from about 2 to about 8. In yet another embodiment, the number of paddles 1136 is 6.

Paddles 1136 help move the material and medium towards the second screen section 1102B, as well as the discharge outlet 1120, so as to further separate and dry the material. Each paddle 1136 can optionally include one or more rakes 1150. In one embodiment, the number of rakes 1150 can range from about 4 to about 16. The number of rakes 1150 and paddles 1136 can be modified depending on the amount of solids in the feed, for example.

A gap between screen 1102 and paddles 1136 can range from about 0.25 to 0.65 inch. A smaller gap gives a drier cake with higher capacity and purer fiber. A larger gap gives a wetter cake with lower capacity and purer protein stream in the slurry passing through the screen openings.

A motor 1152 is operatively coupled to rotation of a drive shaft 1170 positioned about central axis 1114. A controller can be operatively coupled to the motor 1152 for controlling the rotational speed of drive shaft 1170, which can be constant or variable. Drive shaft 1170 is operatively coupled to shaft 1132 to effect a rotational motion of shaft 1132 by a suitable motor 1152.

In some embodiments, rotation of shaft 1132 can result from other motive force-generating devices. For example, one end of shaft 1132 can be operatively coupled to an electric motor, such as via a suitable belt or by direct drive, so as to cause the shaft 1132 to rotate about the central axis 1114. In one embodiment, the controller can be a computer, which can control the rotational speed of the shaft 1132.

The rotational speed of shaft 1132 can be selectively varied depending on the specific application. In one embodiment, shaft 1132 can be rotated at a speed (e.g., revolutions per minute) that can range from about 100 to about 2000 RPM. In another embodiment, the speed can range from about 400 to about 1000 RPM. In another embodiment, the speed can range from about 500 to about 900 RPM. A higher speed provides higher capacity but consumes more power. Those of ordinary skill in the art will recognize that these values are exemplary and the speeds may be selected and optimized to meet the needs of a particular application.

Shaft 1132 further includes a washing water inlet 1156 that is centrally situated within and extends substantially along the length of the shaft 1132. Washing water inlet 1156 is adapted to receive wash water therethrough from a desired source. Shaft 1132 also has a plurality of liquid outlets 1158 associated with liquid inlet 1156 and are spaced apart along substantially the length of shaft 1132 within the first, second, third and fourth zones 1116A, 1116B, 1116C and 1116D for introducing wash water therein. One or more of outlets 1158 may be controlled or eliminated altogether so as to prevent or reduce the amount of wash water entering into any one zone 1116A, 1116B, 1116C and 1116D. Additionally, a counter current washing technique may be employed to save wash water usage.

The paddles 1136 in fourth zone 1116D do a desirable job of producing a drier fiber for maximum liquid medium recovery from the fiber material. It is anticipated that the fiber material that exits the apparatus via discharge chute 1120 can be between approximately 55% and approximately 80%, preferably between 55% and 70% water. This water concentration range represents a significant improvement over conventional systems (e.g., pressure and paddle screen devices), which typically provide fiber material at over about 80% to about 92% water.

Also, one or more removable access panels 1162, which are situated on the top side of the side wall 1122 of the housing 1106, may be provided for accessing the interior of apparatus 1100. A support stands 1173 is provided to support apparatus 1100, as is a bearing housing 1172.

Apparatus 1100 may have a length to diameter (L/D) ratio greater than two. In one embodiment, apparatus 1100 may have a L/D ratio between approximately 2 and 10, and more preferably between 4 and 6. These values are exemplary and those of ordinary skill in the art will recognize other ratios suitable for a particular application can be used.

Drawing 1100 shows a four section screen 1102. However, more screen sections can separate more products to be produced from single machine. The addition of a screen section not only can be used to separate different type of solids, it also can supply more screen surface area for washing and dewatering of larger diameter solids. The length of apparatus 1100 can increase when adding more screen sections.

The critical speed of apparatus 1100 can decrease with longer machine. To solve this critical speed decrease, it can be improved by the design of a larger diameter machine. The larger diameter machine also can give much higher washing capacity. For example, 400 mm paddle screen only has a maximum washing water of 90 GPM, but a 600 mm paddle screen can operate with up to 600 GPM washing water.

The screen types can be varied where smaller particles are allowed through the earlier screens and larger particles are allowed through the later screens. Larger screens can be used in the later stages to allow for more efficient/complete dewatering of the large particles before leaving the machine. The same size screens can be used where there is wash water used in an early stage and no wash water used in a later stage are used, allowing for higher dewatering with good produce recovery.

More chambers (e.g., additional screen sections) allow for more products to be produced from a single machine. The additional screen sections allow for (a) additional dewatering of the large diameter solids, (b) the support the use of both large and small screen diameters, e.g., a substantially larger screen diameter of (e.g., 600 mm) can be used, while the screen diameters of two-section washing paddle machines are typically limited to a maximum diameter of 400 mm; (c) a much larger throughput of the machine, which is typically at least 50% more than a two-section washing paddle machine, and (d) a higher wash water to feed volume (e.g., 1-part wash water to 3-parts feed volume.)

The wash water can be adjusted so each screen section can be fed independent amounts of wash water. Washing the individual sections allows for higher purity materials of different types that can be separated from the whole material. The substantial wash water volume allows for higher volumes of different products to be isolated as well as more purified large diameter particles that stay on the screen surface. The additional wash volumes allow for more tailored products and higher efficiency in the recovery and separation of insoluble and soluble materials of different particle size.

The screen types can be of any design, such as punched hole screens or wedge wire screens. The wedge wire screens can be formed into a cylindrical-like shape at different angles.

Figure 8A:
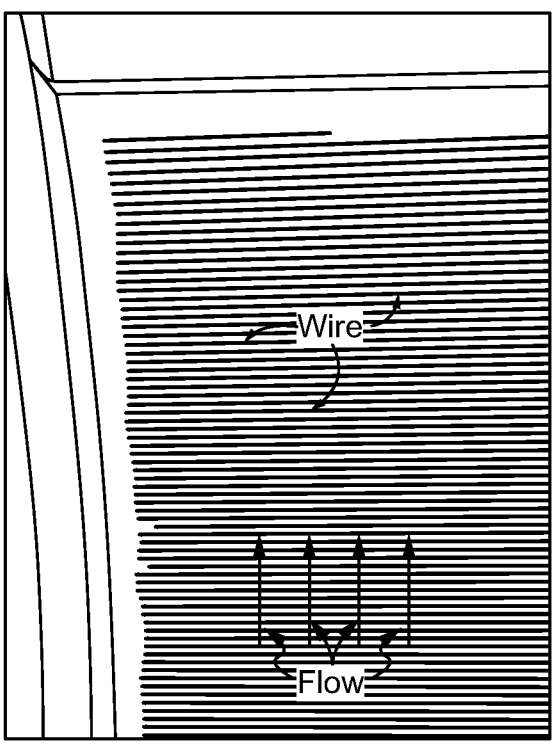
FIGS. 8A and 8B illustrate new paddle screen designs with vertical and horizontal slot design in accordance with some embodiments.

FIG. 8A shows a wedge wire screen with a plurality of parallel slot openings that are perpendicular to a downstream direction of liquid flowing.

Figure 8B:
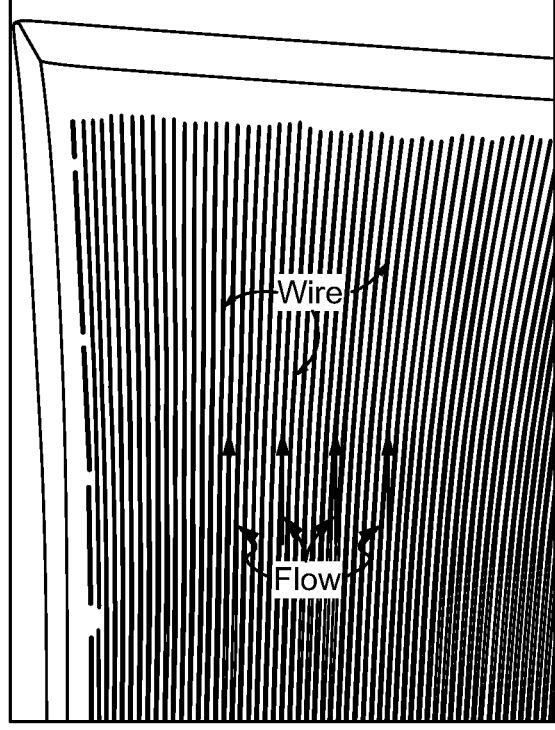

FIG. 8B shows a cylindrical screen that can be formed with a plurality of parallel wires with a plurality of parallel slots openings therebetween, which is assembled parallel to a liquid flow direction. The screens in FIGS. 8A and 8B are able to be manufactured similarly. In other embodiments, the slots of the cylindrical screen can be oriented at any angle between perpendicular slots as shown in the FIG. 8A and parallel slots of FIG. 8B. For example, the slots can be oriented at a 30 degree, a 45 degree, or any other angle to the liquid flow direction.

The parallel perpendicular slots can be used to separate different types of materials. For example, yeast cells, fine fiber and grit. Yeast cells are round with a diameter of about 10 microns. Fiber is typically less than about 50 microns in diameter, but longer than about 200 microns. Grit typically has a square shape with larger than about 250 microns in overall dimension. When the first screen has 50 micron slots perpendicular to flow, the yeast cells will pass through, but the large dimension of the fine fiber will not pass through the slots, which are carried to the next section. When the second section screen has 50 micron slots parallel to flow, the small dimension of the fine fiber will pass through, but the grit will not and will be carried to the next section. If the third section screen is smaller than about 200 microns, the grit will stay within the screen and can be washed and dewatered, etc.

Operation of the apparatus 1100 is further described. To facilitate understanding of various aspects of the invention, operation of apparatus 1100 will be described in the context of fiber filtration in a corn dry mill process. It should be appreciated, however, that apparatus 1100 may be used in a wide range of applications, including grain wet or dry mills. It is not limited in use to either the corn wet mill or dry mill process described herein.

In one embodiment of the presently claimed invention, the linear velocity at which the medium and material is introduced into apparatus 1100 at inlet 1118 can be the same as, or close to the same as the tangential linear velocity of the outer edges of vanes 1136, which act as an auger at the surface of screen 1102. Matching the speeds can help conserve power consumption and maximize separation of the medium and material.

The concavity of the end of the shaft 1132, adjacent to an opening of feed inlet 1118, helps direct the slurry into first zone 1116A and ultimately between shaft 1132, acting as the auger, first screen section 1102A, and the open cavities between vanes 1136. Wash water can also be directed into this space from outlets 1158 on shaft 1132. The wash water effectively washes the fiber.

With the rotation of the shaft 1132 and, thus, paddles (vanes) 1136, the slurry is moved in a downstream direction along length L of first zone 1116A. Fiber is filtered from the slurry, by allowing the water, starch, gluten, and possibly other of the smallest constituents of the slurry to pass through first screen section 1102A and drain into hopper 1126A. Fibers and possibly relatively larger constituents of the slurry are retained within screen 1102 of apparatus 1100.

The fiber containing slurry is eventually caused by paddles 1136 to flow downstream along the multiple screen sections. Washing and/or dewatering can occur in second zone 1116B. Wash water can be directed therein via outlets 1158 on shaft 1132. Due to the rotation of paddles 1136, the wet fiber is moved along length L of second zone 1116B. The fiber is further dewatered and filtered from the liquid medium, thereby allowing any additional water and small constituents, such as starch, gluten, and possibly other relatively small constituents of the slurry to pass through second screen section 1102B and drain into second hopper 1126B.

The washed fiber is then moved into third zone 1116C. Removal of any small particles can continue with additional washing in third section 1116C. Further dewatering can occur in fourth screen section 1116D, while the fiber makes its way towards discharge chute 1120.

A concavity of the end of shaft 1132 adjacent discharge chute 1120 helps direct the de-watered fiber into chute 1120. At the end of fourth zone 1116D, the fiber has been sufficiently concentrated. For example, in one embodiment, the fiber is between about 55% and about 85% water at the end of the fourth zone 1116D. In another embodiment of the invention, the fiber is between about 65% and about 75% water at the end of the third zone 1116D.

The washed and filtered fiber exits via discharge chute 1120. When the fiber exits chute 1120, the fiber may be transported to a remote site and further processed to result in a desired product. Moreover, the slurry that passes through screen 1102, as well any wash water, starch and/or gluten, may also be further processed.

The various features of apparatus 1100 culminate in a synergistic effect. For example, one or more of the features allow apparatus 1100 to be a single, self-contained device that performs both the initial filtering of the liquid medium to remove the desired filtered material, and additional washing/dewatering of the material to remove additional constituents, such as additional starch and/or gluten, therefrom. Apparatus 1100 can also reduce the capital costs of the device, the labor and associated costs for maintaining the device, and the operating costs (e.g., use less water, etc.).

One or more of the features of apparatus 1100 also allow the dewatered material to exit in a drier condition as compared to existing filtration systems.

Providing a drier product results in less wash water required for a given purity level of fiber. Also, drier product may result in additional benefits.

In the process 500 of FIG. 5, the liquefied starch loss in pure fiber is low, which is normally less than 1% in fiber by weight. The loss can be less than 0.4% by adding one more paddle screen at the Step 506 in the FIG. 5A in the process 500A. Every additional paddle screen washing step will decrease liquefied starch loss about 60%. Numbers of washing paddle screen step can be chosen depending on liquefied starch loss in pure fiber. In general, 2 or 3 stages are used.

At the Step 106, the decanter that is used on the whole stillage separation only has 3000 G force, which can only remove/recover corn proteins. So the protein meal from the protein dryer at the Step 501 mainly contains germ/corn protein. The yeast protein and fine germ protein cannot be removed in the whole stillage decanter at the Step 106, which come out as decanter overflow and mostly mix with oil as oil/protein emulsion in the thin stillage.

Figure 6:
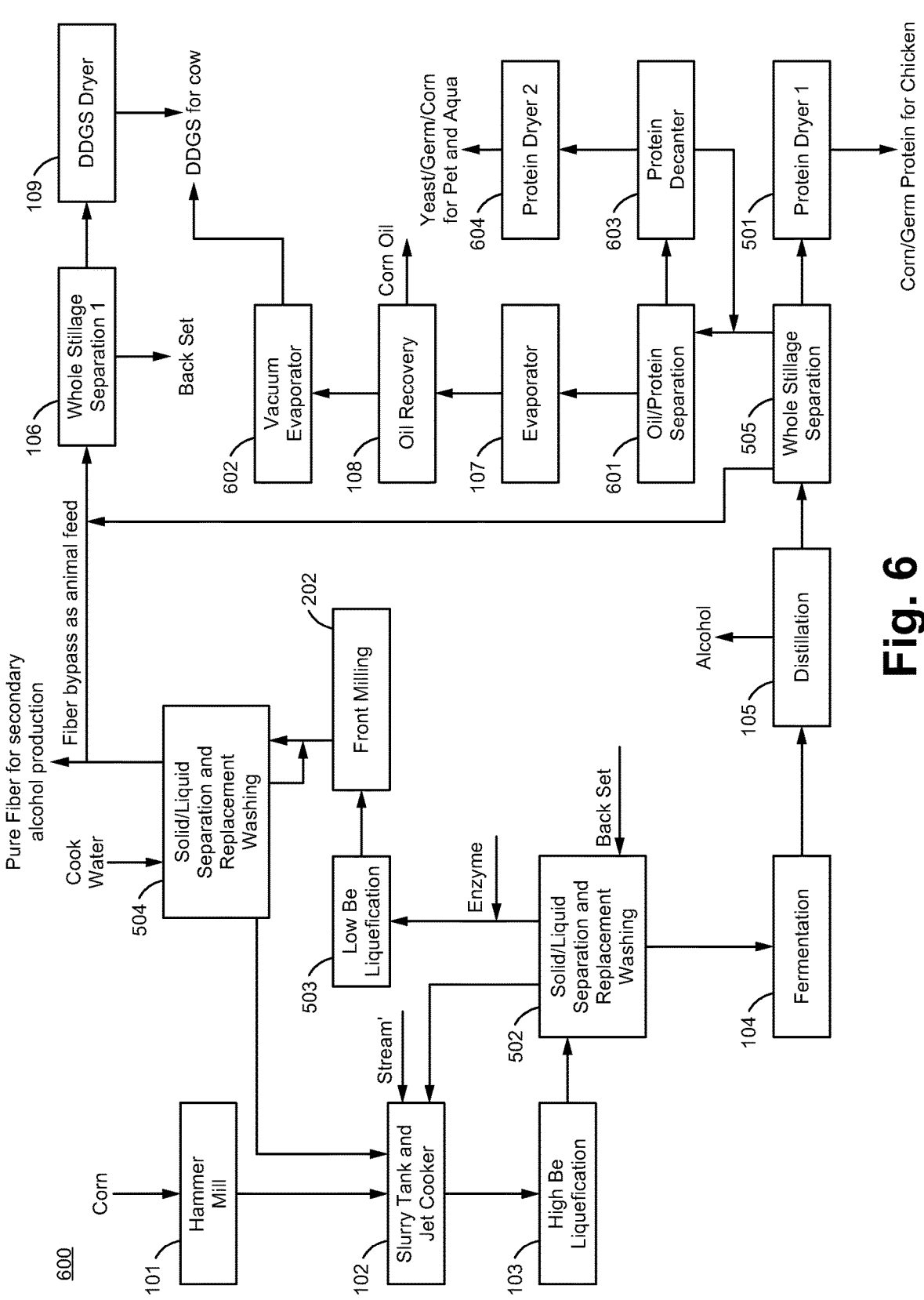
FIG. 6 illustrates a two-stage liquefication process with fiber bypass and two protein feed in accordance with some embodiments.

In the process 600 of FIG. 6, a special power saving nozzle centrifuge with more than 6000G is used to break up oil/protein emulsion and is used to separate oil as a light phase with protein in the heavy phase at a Step 601. As shown in FIG. 6, the front-end process with hammer mill step 101, slurry tank with jet cooker step 102, and two (high/low Be) liquefication steps 103 and 503, plus two solid/liquid separation with high rate replace washing steps 502 and 504 plus wet grind step 202 are the same as process 500 in the FIG. 5. The back end fermentation step 104, distillation step 105, whole stillage separation step 106 and 505 and protein dryer step 501 are same as process 500 in FIG. 5.

The overflow from whole stillage separation step 505 contains oil and fine protein mainly yeast protein send to high G force disc nozzle centrifuge to break oil/protein emulsion and produce very clean, thin stillage containing less than 2% spin solid volume as light phase and more than 30% spin protein solid volume as heavy phase.

This high concentration protein slurry feed to protein decanter step 603 to produce about to 25% DS protein wet protein cake. The overflow from protein decanter contains some fine protein (about 6% spin volume) will recycle back as nozzle centrifuge feed to capture fine protein in second run. This feature increases the oil and protein yield with less HP consumption and lower capital investment.

The overflow from the oil/protein separation at the Step 601 is very a clean thin stillage, which can be evaporated to around 30% DS in exiting the evaporator at the Step 107, which is followed by an oil recovery step at the Step 108 to recover valuable corn oil. The de-oiled syrup can be further concentrated in vacuum force recycle evaporator at the Step 602 up to 85% DS syrup, which can bypass dryer and to be mixed with a super dry material (around 7% moisture) after dryer to form a high nutrient DDGS. The syrup contains a lot of nutrients (such as vitamins) from yeast broth, which can be destroyed if it is in a high temperature dryer at the Step 109, so the dryer step can be skipped in some embodiments.

The process 600 with oil/protein separation step 601 and protein dewater step 603 to increase oil yield up to 1.4 lb./Bu and produce around 2 lb./Bu very high value yeast/germ protein for house pet and aqua feed, and extra clean, thin stillage, which can be concentrated up to 85% DS syrup and bypass dryer to form a high nutrient DDGS product for cattle. The process 600 also produces about 3 to 4 lb./Bu corn protein for chicken.

Figure 7:
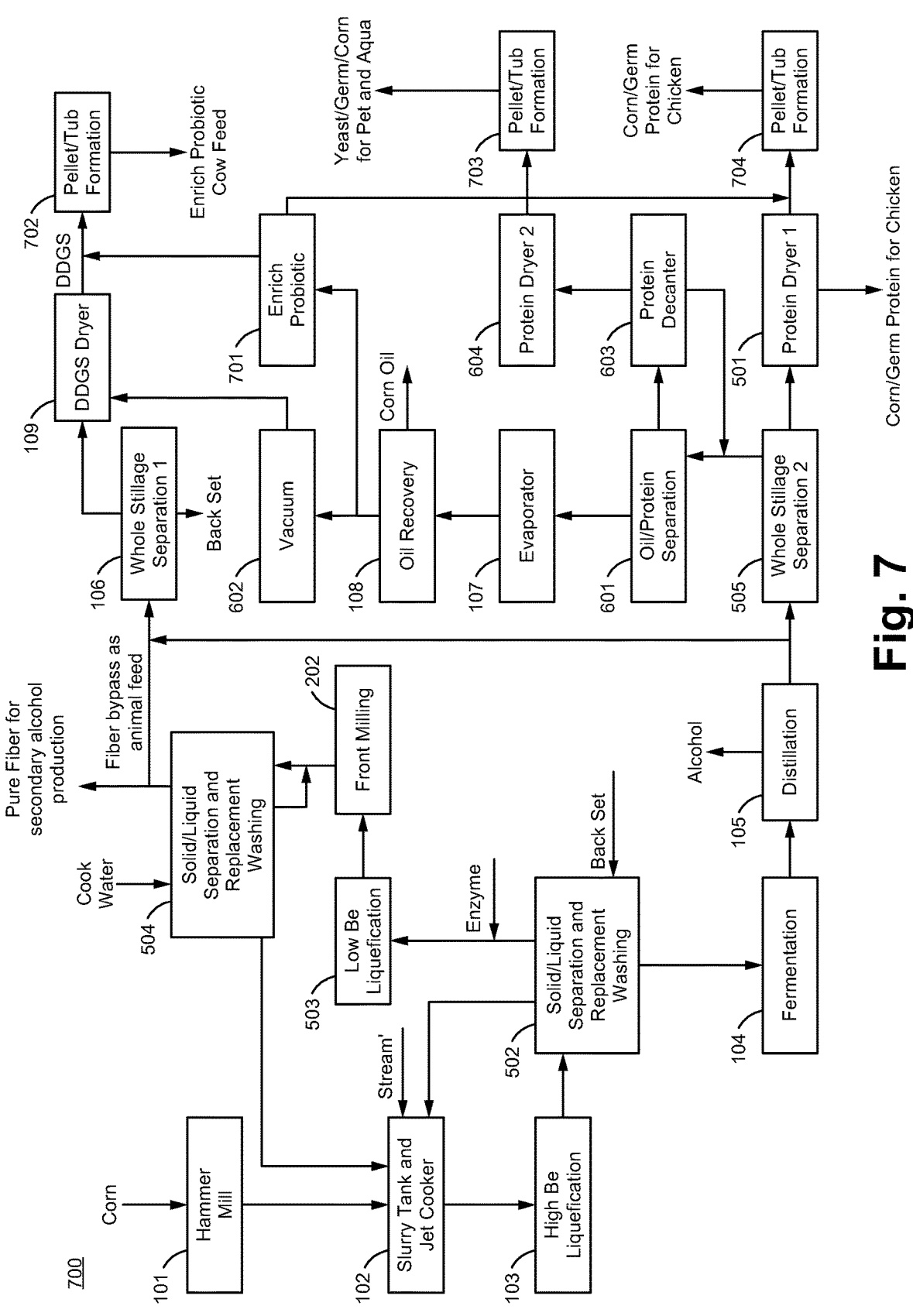
FIG. 7 illustrates a two-stage liquefication process with fiber bypass and three enrich probiotic animal feeds in accordance with some embodiments.

The process 600 can be further improved by adding enrich probiotic Step 701 as shown in the FIG. 7, process 700. About 10 to 15% of de-oil syrup with about 30% DS is continuously fed to a secondary fermentation tank in the enrich/probiotic step 701. A mixture of lactic acid produce culture such as *lactobacillus-plantarum, Lactobacillus amylovorus, Lactobacillus mucosae, Lactobacillus fermentum* are added to continue secondary fermentation tank step 701 to convert resident sugar in syrup to lactic acid. With about an average one day fermentation time, the enriched syrup from this continue fermentation tank will has 20% lactic acid in dry base and 10^-9 CFU probiotic unit. This enriched probiotic can be used as a bonding agent, which is mixed with any dry animal feed to form enrich probiotic animal, as shown in the Step 702, as an enrich probiotic cow feed, in step 703 as enrich probiotic pet and aqua feed, in step 704 as enrich probiotic chicken feed.

Corn is main feed stock for dry mill process in USA. Brazil expects a gradual switch from sugarcane to corn in the years to come. Rice can be another good source of feed stock in South Asia area. The byproducts, oil and protein, can be used for human consumption.

Figure 9:
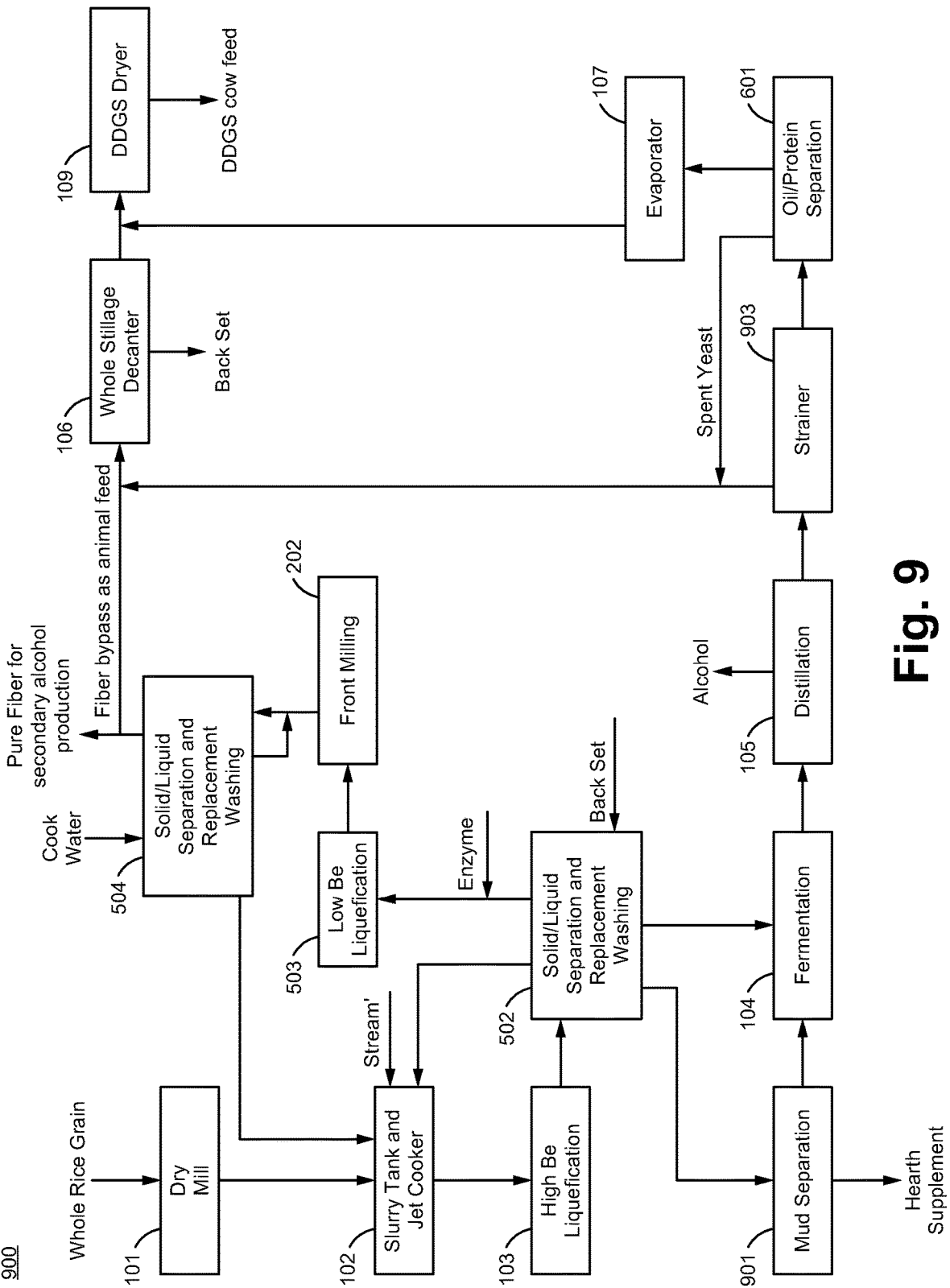
FIG. 9 illustrates a whole rice grain with LTFMT process for producing healthy food supplement and alcohol for human consumption in accordance with some embodiments.

In FIG. 9, the process 900 uses rice as feed stock for dry mill process to recover valuable byproduct (oil and protein) for human consumption in accordance with some embodiments. The whole grain rice with hull can used as feed stock or the waste stream from exiting dehull operation as feed stock. The whole rice grains are going through a dry mill at the Step 101 to be broken up, which are then sent to a slurry tank and jet cooker at a Step 102. The content from the Step 102 is sent to a liquefied tank at a Step 103 to liquefy the starch. The liquefied slurry with hull, germ, protein, and fine fiber are fed to solid/liquid separation with a high-rate replacement washing at a Step 502 for separating/washing larger solid particle such as hull with starch as a wet cake. The fine solids (such as germ, protein, and fine fiber with liquefied starch) are in the filtrate. The filtrate stream goes to mud separation at a Step 901 to recover mud (oil/germ/protein mixture) for human consumption as a health supplement. The filtrate from the 1^st section screen is sent to a fermenter at a Step 104 for alcohol production followed by distillation at the Step 105. Referring back to the Step 502, the back set stream is used as displacement washing water to wash off liquefied starch before sending hull with any attached starch to a low Be liquefication tank at a Step 503.

After the Step 503, the attached starch will be further liquefied with optional wet milling at the Step 202 to ensure all starch attached to hull is liquefied before sending to solid/liquid separation with a high-rate displacement washing at the Step 504. At the Step 504, the cook water is used as displacement washing water to washing off any liquefied starch to produce pure fiber for paper production or DDGS cow feed by mixing the content from the Step 504 with syrup after dryer. From the Step 106, the filtrate with liquefied starch are used as cook water to be supplied to the slurry tank at the Step 102.

At the Step 106, the whole stillage in the backend is sent to a continuous rotary strainer to remove any large solid particles and to split the flow, about 25% of the whole stillage with large solid particle mixture is mixed with high concentrate syrup from an evaporator at the Step 107 to be sent to a DDGS dryer at a Step 109 to produce DDGS, which can be used as cow feed. At the Step 106, the concentrate from the whole stillage decanter is used as back set as washing water on solid/liquid separation and replacement washing at the Step 502. Another split flow from whole stillage goes to oil/protein separation at a Step 603 to concentrate spent yeast (not shown). The concentrate spent yeast from underflow of oil/protein separation at a Step 601 is sent to whole stillage decanter at a Step 106. The overflow from oil/protein separation at the Step 601 as thin stillage is sent to evaporator step 107 to boil off water generating a highly concentrated syrup, which is mixed with the wet DDG cake from the Step 106 to be sent to the DDGS dryer at the Step 109 to produce DDGS cow feed.

Figure 10:
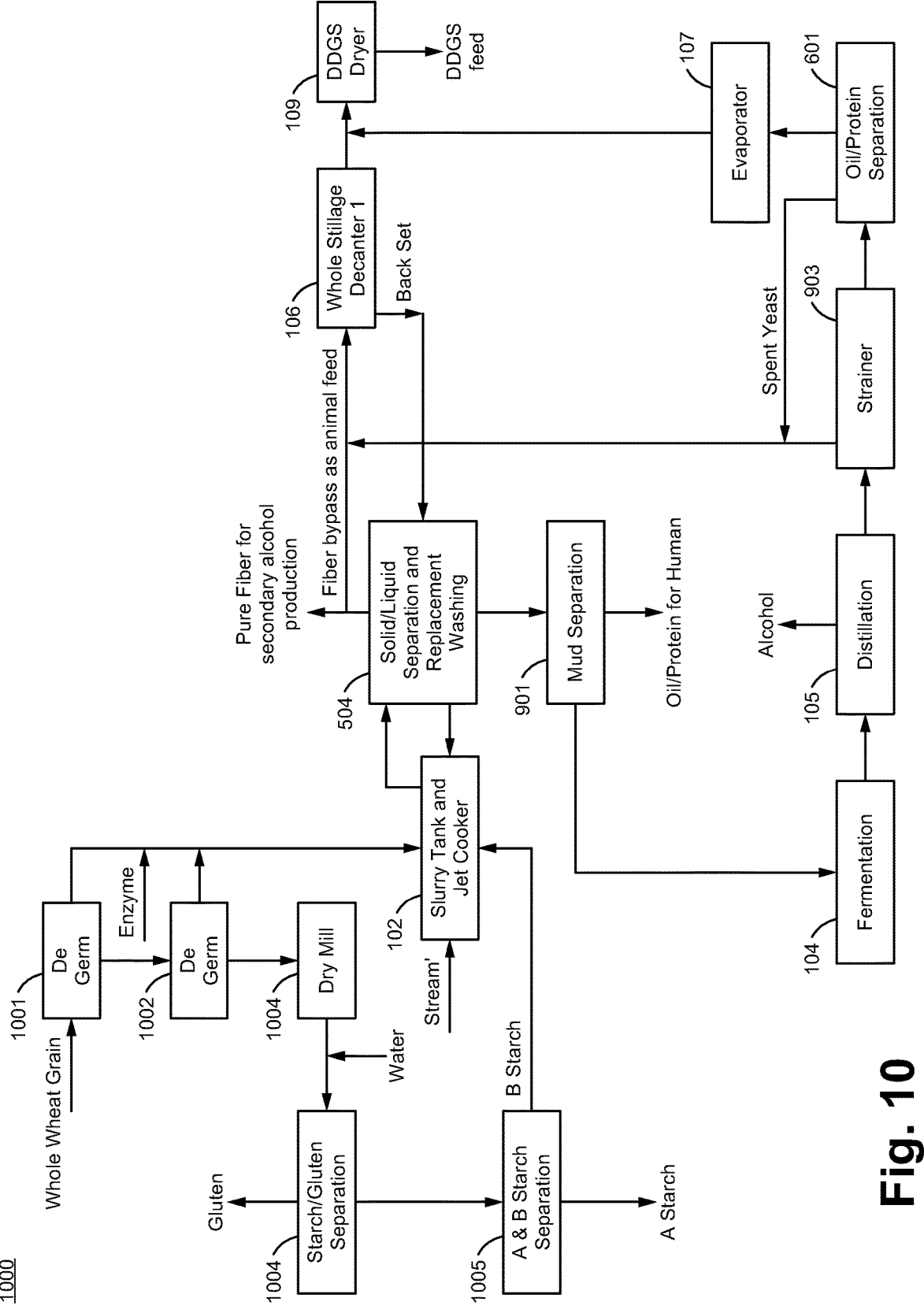
FIG. 10 illustrates a whole wheat grain with LTFMT process for producing oil, protein and alcohol for human consumption in accordance with some embodiments.

In the FIG. 10, Process 1000 shows other grains, like wheat, also can produce oil/protein healthy food and alcohol for human consumption. The whole wheat grains go through typical dehulling at a Step 1001, degumming at a Step 1002, dry milling at a Step 1003, germ/starch separating at a Step 1004 and A and B starch separating at a Step 1005. All waste streams containing starch B are sent to a slurry tank at the Step 102 with filtrate from solid/liquid separation and displacement washing at a Step 504 as cook water. The liquefied starch slurry is fed to solid/liquid separating at a Step 504 to separate Coarse fiber (hull) and washing off liquefied starch and produce pure fiber for secondary alcohol production or feed stock for paper industry by using a backset stream from a whole stillage decanter at the Step 106 using concentrate as washing liquid. The first filtrate from solid/liquid separate at the Step 504 with liquefied starch and oil/germ/protein is sent to a mud centrifuge to separate mud (oil/germ/protein mixture) as light phase and clean liquefied starch as a heavy phase. The mud with oil and protein in grain can be used as health supplement for human consumption. This liquefied starch goes through fermentation Step 104 and distillation Step 105 to produce alcohol for human consumption. The whole stillage from distillation step 106 is sent to a strainer at the Step 903 and oil/protein separation at a Step 601 to produce very clean, thin stillage. At the Step 601, the thin stillage is sent to an evaporator at a Step 107 and high concentrate spent yeast as heavy phase, which is sent to the Step 106. At the Step 107, the thin stillage boils off water and produces high concentrate syrup, which is mixed with wet cake from whole stillage decanter at the Step 106. The mixture is dried in a DDGS dryer at the Step 109 to produce DDGS as cow feed.

Two liquefication process with fiber bypass at the front-end and four animal feed on back end with corn as feed stock are disclosed in the process 500, 500A, 600, and 700 of FIGS. 5, 5A, 6 and 7 respectively. Other feed stock also can apply as shown in the process 900 of FIG. 9 including rice that is used as feedstock. The process 1000 of FIG. 10 uses wheat as feed stock. Any waste stream from any food process plant contains fiber, oil, and protein all can use this technology disclosed herein to solve earth climate change problems.

In utilization, the processes are used to release more oil and starch in the corn feedstocks resulting in increased alcohol yield up to 3% and the increased oil yield up to 1.4 lb./bu.

In operation, two liquefication stages and two solid/liquid separation and replacement washing steps plus a wet milling step are further incorporated to improve typical dry milling processes.

I claim:
1. A dry milling process comprising:
a liquifying starch in floury endosperm from milled corn kernels making a liquefied starch slurry in a first liquefication tank having a slurry of 20-27 Be;
b. performing solid/liquid separation forming a liquid portion and a solid portion;
c. sending the liquid portion containing the starch in the floury endosperm to a fermenter;
d. sending the solid portion for reducing a density of the slurry of 20-27 Be to a slurry <5 Be by using a washing water from backset stream after the first liquefication tank and before a second liquefication tank, wherein the solid portion comprises grit and germ particles;
e. soaking, cooking, or degrading protein using a protein cell wall degrading enzyme in the second liquefication tank having the slurry <5 Be, wherein the protein cell wall degrading enzyme contains cellulase, protease, cell wall degrading enzymes, or a combination of thereof;

f. performing wet grinding after the second liquefication tank to break up and release starch in horny endosperm and oil; and g. liquefying starch in the horny endosperm in the second liquefication tank having the slurry <5 Be.

2. The dry milling process of claim 1, further comprising performing a holding time on the first liquefication tank between 1 to 2 hours.

3. The dry milling process of claim 1, wherein the soaking, cooking, or degrading the protein is performed for 2 to 4 hours.

4. The dry milling process of claim 1, further comprising performing a first solid/liquid separation between the liquefying starch at the first liquefication tank and the soaking, cooking, or degrading protein at the second liquefication tank.

5. The dry milling process of claim 4, further comprising using a back set stream as the washing water to perform a displacement washing at the first solid/liquid separation.

6. The dry milling process of claim 5, further comprising performing the displacement washing at the first solid/liquid separation until a content in a first paddle screen becoming the slurry <5 Be.

7. The dry milling process of claim 1, further comprising performing a second solid/liquid separation after the soaking, cooking, or degrading protein at the second liquefication tank.

8. The dry milling process of claim 7, further comprising using a cook water as washing water in a second paddle screen to wash off small germ and grit particles.

9. The dry milling process of claim 8, further comprising producing DDG in a form of a wet cake by mixing pure fiber from the second paddle screen with a portion of a whole stillage.

10. A dry milling process comprising:

a. liquefying starch in floury endosperm from milled corn kernels making a liquefied starch slurry in a first liquefication tank having a slurry of 20-27 Be;

b. performing solid/liquid separation forming a liquid portion and a solid portion;

c. sending the liquid portion containing the starch in the floury endosperm to a fermenter;

d. sending the solid portion for reducing a density of the slurry of 20-27 Be to a slurry <5 Be by using a washing water from backset stream after the first liquefication tank and before a second liquefication tank, wherein the solid portion comprises grit and germ particles;

e. degrading protein using a protein cell wall degrading enzyme in the second liquefication tank having the slurry <5 Be, wherein the protein cell wall degrading enzyme contains cellulase, protease, cell wall degrading enzymes, or a combination of thereof;

f. performing wet grinding after the second liquefication tank to break up and release starch in horny endosperm and oil; and g. liquefying starch in the horny endosperm in the second liquefication tank having the slurry <5 Be.

* * * * *